US012697124B2

(12) United States Patent　(10) Patent No.:　US 12,697,124 B2
Inouye et al.　(45) Date of Patent:　Aug. 4, 2026

(54) MEDICAL DEVICE FOR OCCLUDING A LEFT ATRIAL APPENDAGE

(71) Applicant: BOSTON SCIENTIFIC SCIMED, INC., Maple Grove, MN (US)

(72) Inventors: Joshua Mark Inouye, Brooklyn Park, MN (US); Levi Joel Wolterstorff, Saint Paul, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 351 days.

(21) Appl. No.: 18/215,639

(22) Filed: Jun. 28, 2023

(65) Prior Publication Data

US 2024/0000457 A1　Jan. 4, 2024

Related U.S. Application Data

(60) Provisional application No. 63/356,535, filed on Jun. 29, 2022.

(51) Int. Cl.
*A61B 17/12*　(2006.01)
*A61B 17/00*　(2006.01)

(52) U.S. Cl.
CPC .. *A61B 17/12122* (2013.01); *A61B 17/12172* (2013.01); *A61B 2017/00632* (2013.01); *A61B 17/12177* (2013.01)

(58) Field of Classification Search
CPC ........ A61B 17/12122; A61B 17/12172; A61B 17/12177; A61B 2017/00632; A61B 2017/12095
See application file for complete search history.

(56) References Cited

U.S. PATENT DOCUMENTS

| 178,283 A | 6/1876 | French |
| 1,967,318 A | 7/1934 | Monahan |

(Continued)

FOREIGN PATENT DOCUMENTS

| CN | 1399571 A | 2/2003 |
| CN | 202143640 U | 2/2012 |

(Continued)

OTHER PUBLICATIONS

International Search Report and Written Opinion dated Sep. 27, 2023 for International Application No. PCT/US2023/026479.

(Continued)

*Primary Examiner* — Paula J Stice

(74) *Attorney, Agent, or Firm* — Seager, Tufte & Wickhem LLP

(57) ABSTRACT

A medical implant for occluding a left atrial appendage includes an expandable framework configured to shift between a first configuration and a second configuration, and an occlusive element secured to the expandable framework. The expandable framework includes a plurality of interconnected struts extending from a proximal hub. The plurality of interconnected struts includes a first plurality of struts and a second plurality of struts. In the second configuration, the first plurality of struts each extend radially along a first strut path from the proximal hub to one of a first plurality of strut intersections, and the second plurality of struts each extend radially along a second strut path from the proximal hub to one of a second plurality of strut intersections. In the second configuration, the first plurality of struts forms a depression in the expandable framework and the second plurality of struts extends into the depression.

19 Claims, 8 Drawing Sheets

(56)                References Cited

U.S. PATENT DOCUMENTS

| | | | |
|---|---|---|---|
| 3,402,710 A | 9/1968 | Paleschuck |
| 3,540,431 A | 11/1970 | Mobin-Uddin |
| 3,557,794 A | 1/1971 | Van Patten |
| 3,638,652 A | 2/1972 | Kelley |
| 3,811,449 A | 5/1974 | Gravlee et al. |
| 3,844,302 A | 10/1974 | Klein |
| 3,874,388 A | 4/1975 | King et al. |
| 4,007,743 A | 2/1977 | Blake |
| 4,108,420 A | 8/1978 | West et al. |
| 4,175,545 A | 11/1979 | Termanini |
| 4,309,776 A | 1/1982 | Berguer |
| 4,341,218 A | 7/1982 | Ü |
| 4,364,392 A | 12/1982 | Strother et al. |
| 4,425,908 A | 1/1984 | Simon |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand et al. |
| 4,665,906 A | 5/1987 | Jervis |
| 4,681,588 A | 7/1987 | Ketharanathan et al. |
| 4,710,192 A | 12/1987 | Liotta et al. |
| 4,718,417 A | 1/1988 | Kittrell et al. |
| 4,759,348 A | 7/1988 | Cawood et al. |
| 4,781,177 A | 11/1988 | Lebigot |
| 4,793,348 A | 12/1988 | Palmaz |
| 4,827,907 A | 5/1989 | Tashiro |
| 4,832,055 A | 5/1989 | Palestrant |
| 4,873,978 A | 10/1989 | Ginsburg |
| 4,917,089 A | 4/1990 | Sideris |
| 4,921,484 A | 5/1990 | Hillstead |
| 4,960,412 A | 10/1990 | Fink |
| 4,966,150 A | 10/1990 | Etienne et al. |
| 4,998,972 A | 3/1991 | Chin et al. |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,171,259 A | 12/1992 | Inoue |
| 5,171,383 A | 12/1992 | Sagaye et al. |
| 5,176,692 A | 1/1993 | Wilk et al. |
| 5,192,301 A | 3/1993 | Kamiya et al. |
| 5,211,658 A | 5/1993 | Clouse |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,279,539 A | 1/1994 | Bohan et al. |
| 5,284,488 A | 2/1994 | Sideris |
| 5,304,184 A | 4/1994 | Hathaway et al. |
| 5,306,234 A | 4/1994 | Johnson |
| 5,312,341 A | 5/1994 | Turi |
| 5,329,942 A | 7/1994 | Gunther et al. |
| 5,334,217 A | 8/1994 | Das |
| 5,344,439 A | 9/1994 | Otten |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,331 A | 3/1995 | Himpens et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,427,119 A | 6/1995 | Swartz et al. |
| 5,433,727 A | 7/1995 | Sideris |
| 5,443,454 A | 8/1995 | Tanabe et al. |
| 5,443,478 A | 8/1995 | Purdy et al. |
| 5,451,235 A | 9/1995 | Lock et al. |
| 5,454,365 A | 10/1995 | Bonutti |
| 5,464,408 A | 11/1995 | Duc |
| 5,469,867 A | 11/1995 | Schmitt |
| 5,490,856 A | 2/1996 | Person et al. |
| 5,497,774 A | 3/1996 | Swartz et al. |
| 5,499,975 A | 3/1996 | Cope et al. |
| 5,499,995 A | 3/1996 | Teirstein |
| 5,522,790 A | 6/1996 | Voll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,558,093 A | 9/1996 | Pomeranz et al. |
| 5,558,652 A | 9/1996 | Henke |
| 5,569,204 A | 10/1996 | Cramer et al. |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,345 A | 10/1997 | Euteneuer |
| 5,681,347 A | 10/1997 | Cathcart et al. |
| 5,683,411 A | 11/1997 | Kavteladze et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,704,910 A | 1/1998 | Humes |
| 5,709,224 A | 1/1998 | Behl et al. |
| 5,709,704 A | 1/1998 | Nott et al. |
| 5,709,707 A | 1/1998 | Lock et al. |
| 5,722,400 A | 3/1998 | Ockuly et al. |
| 5,724,975 A | 3/1998 | Negus et al. |
| 5,725,512 A | 3/1998 | Swartz et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,880 A | 5/1998 | Banas et al. |
| 5,749,883 A | 5/1998 | Halpern |
| 5,749,894 A | 5/1998 | Engelson |
| 5,766,219 A | 6/1998 | Horton |
| 5,766,246 A | 6/1998 | Mulhauser et al. |
| 5,769,816 A | 6/1998 | Barbut et al. |
| 5,776,097 A | 7/1998 | Massoud |
| 5,776,162 A | 7/1998 | Kleshinski |
| 5,782,860 A | 7/1998 | Epstein et al. |
| 5,785,679 A | 7/1998 | Abolfathi et al. |
| 5,800,454 A | 9/1998 | Jacobsen et al. |
| 5,800,457 A | 9/1998 | Gelbfish |
| 5,800,512 A | 9/1998 | Letnz et al. |
| 5,807,261 A | 9/1998 | Benaron et al. |
| 5,810,874 A | 9/1998 | Lefebvre |
| 5,814,028 A | 9/1998 | Swartz et al. |
| 5,814,029 A | 9/1998 | Hassett |
| 5,814,064 A | 9/1998 | Daniel |
| 5,820,591 A | 10/1998 | Thompson et al. |
| 5,823,198 A | 10/1998 | Jones et al. |
| 5,830,228 A | 11/1998 | Knapp et al. |
| 5,833,673 A | 11/1998 | Ockuly et al. |
| 5,836,913 A | 11/1998 | Orth et al. |
| 5,836,968 A | 11/1998 | Simon et al. |

(56)　　　　References Cited

U.S. PATENT DOCUMENTS

| | | | |
|---|---|---|---|
| 5,840,027 A | 11/1998 | Swartz et al. | |
| 5,843,118 A | 12/1998 | Sepetka et al. | |
| 5,846,260 A | 12/1998 | Maahs | |
| 5,846,261 A | 12/1998 | Kotula et al. | |
| 5,848,969 A | 12/1998 | Panescu et al. | |
| 5,849,005 A | 12/1998 | Garrison et al. | |
| 5,851,232 A | 12/1998 | Lois | |
| 5,853,422 A | 12/1998 | Huebsch et al. | |
| 5,855,597 A | 1/1999 | Jayaraman | |
| 5,865,791 A | 2/1999 | Whayne et al. | |
| 5,865,802 A | 2/1999 | Yoon et al. | |
| 5,868,702 A | 2/1999 | Stevens et al. | |
| 5,868,708 A | 2/1999 | Hart et al. | |
| 5,876,367 A | 3/1999 | Kaganov et al. | |
| 5,879,296 A | 3/1999 | Ockuly et al. | |
| 5,879,366 A | 3/1999 | Shaw et al. | |
| 5,882,340 A | 3/1999 | Yoon | |
| 5,885,258 A | 3/1999 | Sachdeva et al. | |
| 5,891,558 A | 4/1999 | Bell et al. | |
| 5,895,399 A | 4/1999 | Barbut et al. | |
| 5,902,289 A | 5/1999 | Swartz et al. | |
| 5,904,680 A | 5/1999 | Kordis et al. | |
| 5,904,703 A | 5/1999 | Gilson | |
| 5,906,207 A | 5/1999 | Shen | |
| 5,910,154 A | 6/1999 | Tsugita et al. | |
| 5,911,734 A | 6/1999 | Tsugita et al. | |
| 5,916,236 A | 6/1999 | Muijs Van de Moer et al. | |
| 5,925,060 A | 7/1999 | Forber | |
| 5,925,063 A | 7/1999 | Khosravi | |
| 5,925,074 A | 7/1999 | Gingras et al. | |
| 5,925,075 A | 7/1999 | Myers et al. | |
| 5,928,192 A | 7/1999 | Maahs | |
| 5,928,260 A | 7/1999 | Chin et al. | |
| 5,931,818 A | 8/1999 | Werp et al. | |
| 5,935,145 A | 8/1999 | Villar et al. | |
| 5,935,147 A | 8/1999 | Kensey et al. | |
| 5,935,148 A | 8/1999 | Villar et al. | |
| 5,941,249 A | 8/1999 | Maynard | |
| 5,941,896 A | 8/1999 | Kerr | |
| 5,944,738 A | 8/1999 | Amplatz et al. | |
| 5,947,997 A | 9/1999 | Pavcnik et al. | |
| 5,951,589 A | 9/1999 | Epstein et al. | |
| 5,951,599 A | 9/1999 | McCrory | |
| 5,954,694 A | 9/1999 | Sunseri | |
| 5,954,767 A | 9/1999 | Pajotin et al. | |
| 5,957,940 A | 9/1999 | Tanner et al. | |
| 5,961,545 A | 10/1999 | Lentz et al. | |
| 5,976,174 A | 11/1999 | Ruiz | |
| 5,980,514 A | 11/1999 | Kupiecki et al. | |
| 5,980,555 A | 11/1999 | Barbut et al. | |
| 5,989,281 A | 11/1999 | Barbut et al. | |
| 5,993,469 A | 11/1999 | McKenzie et al. | |
| 5,993,483 A | 11/1999 | Gianotti | |
| 5,997,557 A | 12/1999 | Barbut et al. | |
| 6,004,280 A | 12/1999 | Buck et al. | |
| 6,004,348 A | 12/1999 | Banas et al. | |
| 6,007,523 A | 12/1999 | Mangosong | |
| 6,007,557 A | 12/1999 | Ambrisco et al. | |
| 6,010,517 A | 1/2000 | Baccaro | |
| 6,010,522 A | 1/2000 | Barbut et al. | |
| 6,013,093 A | 1/2000 | Nott et al. | |
| 6,024,751 A | 2/2000 | Lovato et al. | |
| 6,024,754 A | 2/2000 | Engelson | |
| 6,024,755 A | 2/2000 | Addis | |
| 6,024,756 A | 2/2000 | Huebsch et al. | |
| 6,027,520 A | 2/2000 | Tsugita et al. | |
| 6,033,420 A | 3/2000 | Hahnen | |
| 6,036,720 A | 3/2000 | Abrams et al. | |
| 6,042,598 A | 3/2000 | Tsugita et al. | |
| 6,048,331 A | 4/2000 | Tsugita et al. | |
| 6,051,014 A | 4/2000 | Jang | |
| 6,051,015 A | 4/2000 | Maahs | |
| 6,056,720 A | 5/2000 | Morse | |
| 6,063,070 A | 5/2000 | Eder | |
| 6,063,113 A | 5/2000 | Kavteladze et al. | |
| 6,066,126 A | 5/2000 | Li et al. | |
| 6,068,621 A | 5/2000 | Balceta et al. | |
| 6,074,357 A | 6/2000 | Kaganov et al. | |
| 6,076,012 A | 6/2000 | Swanson et al. | |
| 6,079,414 A | 6/2000 | Roth | |
| 6,080,182 A | 6/2000 | Shaw et al. | |
| 6,080,183 A | 6/2000 | Tsugita et al. | |
| 6,083,239 A | 7/2000 | Addis | |
| 6,090,084 A | 7/2000 | Hassett et al. | |
| 6,096,052 A | 8/2000 | Callister et al. | |
| 6,096,053 A | 8/2000 | Bates et al. | |
| 6,110,243 A | 8/2000 | Wnenchak et al. | |
| 6,123,715 A | 9/2000 | Amplatz | |
| 6,124,523 A | 9/2000 | Banas et al. | |
| 6,132,438 A | 10/2000 | Fleischman et al. | |
| 6,135,991 A | 10/2000 | Muni et al. | |
| 6,136,016 A | 10/2000 | Barbut et al. | |
| 6,139,527 A | 10/2000 | Laufer et al. | |
| 6,139,573 A | 10/2000 | Sogard et al. | |
| 6,152,144 A | 11/2000 | Lesh et al. | |
| 6,152,946 A | 11/2000 | Broome et al. | |
| 6,156,055 A | 12/2000 | Ravenscroft | |
| 6,159,195 A | 12/2000 | Ha et al. | |
| 6,161,543 A | 12/2000 | Cox et al. | |
| 6,168,615 B1 | 1/2001 | Ken et al. | |
| 6,171,329 B1 | 1/2001 | Shaw et al. | |
| 6,179,859 B1 | 1/2001 | Bates et al. | |
| 6,193,739 B1 | 2/2001 | Chevillon et al. | |
| 6,203,531 B1 | 3/2001 | Ockuly et al. | |
| 6,206,907 B1 | 3/2001 | Marino et al. | |
| 6,214,029 B1 | 4/2001 | Thill et al. | |
| 6,221,092 B1 | 4/2001 | Koike et al. | |
| 6,231,561 B1 | 5/2001 | Frazier et al. | |
| 6,231,589 B1 | 5/2001 | Wessman et al. | |
| 6,235,045 B1 | 5/2001 | Barbut et al. | |
| 6,245,012 B1 | 6/2001 | Kleshinski | |
| 6,251,122 B1 | 6/2001 | Tsukernik | |
| 6,258,115 B1 | 7/2001 | Dubrul | |
| 6,267,772 B1 | 7/2001 | Mulhauser et al. | |
| 6,267,776 B1 | 7/2001 | O'Connell | |
| 6,270,490 B1 | 8/2001 | Hahnen | |
| 6,270,530 B1 | 8/2001 | Eldridge et al. | |
| 6,270,902 B1 | 8/2001 | Tedeschi et al. | |
| 6,277,138 B1 | 8/2001 | Levinson et al. | |
| 6,285,898 B1 | 9/2001 | Ben-Haim | |
| 6,290,674 B1 | 9/2001 | Roue et al. | |
| 6,290,708 B1 | 9/2001 | Kugel et al. | |
| 6,312,407 B1 | 11/2001 | Zadno-Azizi et al. | |
| 6,319,251 B1 | 11/2001 | Tu et al. | |
| 6,328,727 B1 | 12/2001 | Frazier et al. | |
| 6,328,755 B1 | 12/2001 | Marshall | |
| 6,342,062 B1 | 1/2002 | Suon et al. | |
| 6,346,116 B1 | 2/2002 | Brooks et al. | |
| 6,346,895 B1 | 2/2002 | Lee et al. | |
| 6,361,545 B1 | 3/2002 | Macoviak et al. | |
| 6,364,895 B1 | 4/2002 | Greenhalgh | |
| 6,368,338 B1 | 4/2002 | Konya et al. | |
| 6,371,971 B1 | 4/2002 | Tsugita et al. | |
| 6,375,670 B1 | 4/2002 | Greenhalgh | |
| 6,391,044 B1 | 5/2002 | Yadav et al. | |
| 6,398,803 B1 | 6/2002 | Layne et al. | |
| 6,402,746 B1 | 6/2002 | Whayne et al. | |
| 6,402,771 B1 | 6/2002 | Palmer et al. | |
| 6,402,779 B1 | 6/2002 | Colone et al. | |
| 6,419,669 B1 | 7/2002 | Frazier et al. | |
| 6,440,152 B1 | 8/2002 | Gainor et al. | |
| 6,443,972 B1 | 9/2002 | Bosma et al. | |
| 6,447,530 B1 | 9/2002 | Ostrovsky et al. | |
| 6,454,775 B1 | 9/2002 | Demarais et al. | |
| 6,458,145 B1 | 10/2002 | Ravenscroft et al. | |
| 6,464,712 B1 | 10/2002 | Epstein et al. | |
| 6,468,291 B2 | 10/2002 | Bates et al. | |
| 6,468,301 B1 | 10/2002 | Amplatz et al. | |
| 6,485,501 B1 | 11/2002 | Green | |
| 6,488,689 B1 | 12/2002 | Kaplan et al. | |
| 6,511,496 B1 | 1/2003 | Huter et al. | |
| 6,514,280 B1 | 2/2003 | Gilson | |
| 6,517,573 B1 | 2/2003 | Pollock et al. | |
| 6,533,782 B2 | 3/2003 | Howell et al. | |

(56) References Cited

U.S. PATENT DOCUMENTS

| | | | |
|---|---|---|---|
| 6,547,760 | B1 | 4/2003 | Samson et al. |
| 6,547,815 | B2 | 4/2003 | Myers |
| 6,551,303 | B1 | 4/2003 | Van Tassel et al. |
| 6,551,344 | B2 | 4/2003 | Thill |
| 6,558,401 | B1 | 5/2003 | Azizi |
| 6,558,405 | B1 | 5/2003 | McInnes |
| 6,558,414 | B2 | 5/2003 | Layne |
| 6,562,058 | B2 | 5/2003 | Seguin et al. |
| 6,569,184 | B2 | 5/2003 | Huter |
| 6,569,214 | B2 | 5/2003 | Williams et al. |
| 6,589,214 | B2 | 7/2003 | McGuckin et al. |
| 6,589,251 | B2 | 7/2003 | Yee et al. |
| 6,599,308 | B2 | 7/2003 | Amplatz |
| 6,602,271 | B2 | 8/2003 | Adams et al. |
| 6,623,508 | B2 | 9/2003 | Shaw et al. |
| 6,641,564 | B1 | 11/2003 | Kraus |
| 6,650,923 | B1 | 11/2003 | Lesh et al. |
| 6,652,555 | B1 | 11/2003 | VanTassel et al. |
| 6,652,556 | B1 | 11/2003 | VanTassel et al. |
| 6,666,861 | B1 | 12/2003 | Grabek |
| 6,689,150 | B1 | 2/2004 | Vantassel et al. |
| 6,699,260 | B2 | 3/2004 | Dubrul et al. |
| 6,699,276 | B2 | 3/2004 | Sogard et al. |
| 6,702,825 | B2 | 3/2004 | Frazier et al. |
| 6,712,836 | B1 | 3/2004 | Berg et al. |
| 6,726,701 | B2 | 4/2004 | Gilson et al. |
| 6,730,108 | B2 | 5/2004 | Van Tassel et al. |
| 6,755,812 | B2 | 6/2004 | Peterson et al. |
| 6,827,737 | B2 | 12/2004 | Hill et al. |
| 6,837,901 | B2 | 1/2005 | Rabkin et al. |
| 6,855,153 | B2 | 2/2005 | Saadat |
| 6,911,037 | B2 | 6/2005 | Gainor et al. |
| 6,932,838 | B2 | 8/2005 | Schwartz et al. |
| 6,942,653 | B2 | 9/2005 | Quinn |
| 6,949,113 | B2 | 9/2005 | Van Tassel et al. |
| 6,958,061 | B2 | 10/2005 | Truckai et al. |
| 6,994,092 | B2 | 2/2006 | van der Burg et al. |
| 7,011,671 | B2 | 3/2006 | Welch |
| 7,014,645 | B2 | 3/2006 | Greene, Jr. et al. |
| 7,037,321 | B2 | 5/2006 | Sachdeva et al. |
| 7,044,134 | B2 | 5/2006 | Khairkhahan et al. |
| 7,097,651 | B2 | 8/2006 | Harrison et al. |
| 7,128,073 | B1 | 10/2006 | van der Burg et al. |
| 7,152,605 | B2 | 12/2006 | Khairkhahan et al. |
| 7,169,164 | B2 | 1/2007 | Borillo et al. |
| 7,179,275 | B2 | 2/2007 | McGuckin, Jr. et al. |
| 7,226,466 | B2 | 6/2007 | Opolski |
| 7,303,526 | B2 | 12/2007 | Sharkey et al. |
| 7,323,002 | B2 | 1/2008 | Johnson et al. |
| 7,597,704 | B2 | 10/2009 | Frazier et al. |
| 7,678,123 | B2 | 3/2010 | Chanduszko |
| 7,695,425 | B2 | 4/2010 | Schweich et al. |
| 7,713,282 | B2 | 5/2010 | Frazier et al. |
| 7,722,641 | B2 | 5/2010 | van der Burg et al. |
| 7,727,189 | B2 | 6/2010 | VanTassel et al. |
| 7,735,493 | B2 | 6/2010 | van der Burg et al. |
| 7,780,694 | B2 | 8/2010 | Palmer et al. |
| 7,799,049 | B2 | 9/2010 | Ostrovsky et al. |
| 7,811,300 | B2 | 10/2010 | Feller, III et al. |
| 7,811,314 | B2 | 10/2010 | Fierens et al. |
| 7,862,500 | B2 | 1/2011 | Khairkhahan et al. |
| 7,927,365 | B2 | 4/2011 | Fierens et al. |
| 7,972,359 | B2 | 7/2011 | Kreidler |
| 8,025,495 | B2 | 9/2011 | Hardert et al. |
| 8,043,329 | B2 | 10/2011 | Khairkhahan et al. |
| 8,052,715 | B2 | 11/2011 | Quinn et al. |
| 8,062,282 | B2 | 11/2011 | Kolb |
| 8,080,032 | B2 | 12/2011 | van der Burg et al. |
| 8,097,015 | B2 | 1/2012 | Devellian |
| 8,221,384 | B2 | 7/2012 | Frazier et al. |
| 8,221,445 | B2 | 7/2012 | van Tassel et al. |
| 8,287,563 | B2 | 10/2012 | Khairkhahan et al. |
| 8,323,309 | B2 | 12/2012 | Khairkhahan et al. |
| 8,388,672 | B2 | 3/2013 | Khairkhahan et al. |
| 8,491,623 | B2 | 7/2013 | Vogel et al. |
| 8,523,897 | B2 | 9/2013 | van der Burg et al. |
| 8,535,343 | B2 | 9/2013 | van der Burg et al. |
| 8,562,509 | B2 | 10/2013 | Bates |
| 8,663,273 | B2 | 3/2014 | Khairkhahan et al. |
| 8,685,055 | B2 | 4/2014 | VanTassel et al. |
| 8,834,519 | B2 | 9/2014 | van der Burg et al. |
| 8,845,711 | B2 | 9/2014 | Miles et al. |
| 9,034,006 | B2 | 5/2015 | Quinn et al. |
| 9,132,000 | B2 | 9/2015 | VanTassel et al. |
| 9,168,043 | B2 | 10/2015 | van der Burg et al. |
| 9,211,124 | B2 | 12/2015 | Campbell et al. |
| 9,445,895 | B2 | 9/2016 | Kreidler |
| 9,554,806 | B2 | 1/2017 | Larsen et al. |
| 9,561,037 | B2 | 2/2017 | Fogarty et al. |
| 9,561,097 | B1 | 2/2017 | Kim et al. |
| 9,629,636 | B2 | 4/2017 | Fogarty et al. |
| 9,730,701 | B2 | 8/2017 | Tischler et al. |
| 9,883,936 | B2 | 2/2018 | Sutton et al. |
| 9,913,652 | B2 | 3/2018 | Bridgeman et al. |
| 9,943,299 | B2 | 4/2018 | Khairkhahan et al. |
| 9,943,315 | B2 | 4/2018 | Kaplan et al. |
| 10,071,181 | B1 | 9/2018 | Penegor et al. |
| 10,076,335 | B2 | 9/2018 | Zaver et al. |
| 10,143,458 | B2 | 12/2018 | Kreidler |
| 2001/0000797 | A1 | 5/2001 | Mazzocchi |
| 2001/0020181 | A1 | 9/2001 | Layne |
| 2001/0034537 | A1 | 10/2001 | Shaw et al. |
| 2001/0037141 | A1 | 11/2001 | Yee et al. |
| 2002/0022860 | A1 | 2/2002 | Borillo et al. |
| 2002/0035374 | A1 | 3/2002 | Borillo et al. |
| 2002/0045931 | A1 | 4/2002 | Sogard et al. |
| 2002/0062133 | A1 | 5/2002 | Gilson et al. |
| 2002/0082638 | A1 | 6/2002 | Porter et al. |
| 2002/0082675 | A1 | 6/2002 | Myers |
| 2002/0099439 | A1 | 7/2002 | Schwartz et al. |
| 2002/0111647 | A1 | 8/2002 | Khairkhahan et al. |
| 2002/0138094 | A1 | 9/2002 | Borillo et al. |
| 2002/0138097 | A1 | 9/2002 | Ostrovsky et al. |
| 2002/0169475 | A1 | 11/2002 | Gainor et al. |
| 2002/0177855 | A1 | 11/2002 | Greene, Jr. et al. |
| 2003/0017775 | A1 | 1/2003 | Dong et al. |
| 2003/0023262 | A1 | 1/2003 | Welch |
| 2003/0023266 | A1 | 1/2003 | Borillo et al. |
| 2003/0057156 | A1 | 3/2003 | Peterson et al. |
| 2003/0060871 | A1 | 3/2003 | Hill et al. |
| 2003/0120337 | A1 | 6/2003 | Van Tassel et al. |
| 2003/0181942 | A1 | 9/2003 | Sutton et al. |
| 2003/0191526 | A1 | 10/2003 | Van Tassel et al. |
| 2003/0195555 | A1 | 10/2003 | Khairkhahan et al. |
| 2003/0204203 | A1 | 10/2003 | Khairkhahan et al. |
| 2003/0208214 | A1 | 11/2003 | Loshakove et al. |
| 2003/0220667 | A1 | 11/2003 | van der Burg et al. |
| 2004/0034366 | A1 | 2/2004 | van der Burg et al. |
| 2004/0049210 | A1 | 3/2004 | VanTassel et al. |
| 2004/0093012 | A1 | 5/2004 | Cully et al. |
| 2004/0098031 | A1 | 5/2004 | van der Burg et al. |
| 2004/0122467 | A1 | 6/2004 | VanTassel et al. |
| 2004/0127935 | A1 | 7/2004 | VanTassel et al. |
| 2004/0158274 | A1 | 8/2004 | WasDyke |
| 2004/0186486 | A1 | 9/2004 | Roue et al. |
| 2004/0215230 | A1 | 10/2004 | Frazier et al. |
| 2004/0220610 | A1 | 11/2004 | Kreidler et al. |
| 2004/0220682 | A1 | 11/2004 | Levine et al. |
| 2004/0230222 | A1 | 11/2004 | van der Burg et al. |
| 2005/0004652 | A1 | 1/2005 | van der Burg et al. |
| 2005/0015109 | A1 | 1/2005 | Lichtenstein |
| 2005/0038470 | A1 | 2/2005 | van der Burg et al. |
| 2005/0049573 | A1 | 3/2005 | Van Tassel et al. |
| 2005/0070952 | A1 | 3/2005 | Devellian |
| 2005/0113861 | A1 | 5/2005 | Corcoran et al. |
| 2005/0125020 | A1 | 6/2005 | Meade et al. |
| 2005/0177182 | A1 | 8/2005 | van der Burg et al. |
| 2005/0203568 | A1 | 9/2005 | Burg et al. |
| 2005/0283186 | A1 | 12/2005 | Berrada et al. |
| 2005/0288704 | A1 | 12/2005 | Cartier et al. |
| 2006/0015136 | A1 | 1/2006 | Besselink |
| 2006/0030877 | A1 | 2/2006 | Martinez et al. |
| 2006/0052816 | A1 | 3/2006 | Bates et al. |
| 2006/0100658 | A1 | 5/2006 | Obana et al. |

(56)                    References Cited

U.S. PATENT DOCUMENTS

| | | |
|---|---|---|
| 2006/0155323 A1 | 7/2006 | Porter et al. |
| 2007/0066993 A1 | 3/2007 | Kreidler |
| 2007/0083227 A1 | 4/2007 | van der Burg et al. |
| 2007/0083230 A1 | 4/2007 | Javois |
| 2007/0150041 A1 | 6/2007 | Evans et al. |
| 2007/0156123 A1 | 7/2007 | Moll et al. |
| 2007/0162048 A1 | 7/2007 | Quinn et al. |
| 2007/0185471 A1 | 8/2007 | Johnson |
| 2008/0275536 A1 | 11/2008 | Zarins et al. |
| 2009/0005803 A1 | 1/2009 | Batiste |
| 2009/0062841 A1 | 3/2009 | Amplatz et al. |
| 2009/0099647 A1 | 4/2009 | Glimsdale et al. |
| 2009/0105747 A1 | 4/2009 | Chanduszko et al. |
| 2009/0112249 A1 | 4/2009 | Miles et al. |
| 2009/0254195 A1 | 10/2009 | Khairkhan et al. |
| 2009/0318948 A1 | 12/2009 | Linder et al. |
| 2010/0004726 A1 | 1/2010 | Hancock et al. |
| 2010/0049238 A1 | 2/2010 | Simpson |
| 2010/0106178 A1 | 4/2010 | Obermiller et al. |
| 2010/0324585 A1 | 12/2010 | Miles et al. |
| 2011/0054515 A1 | 3/2011 | Bridgeman et al. |
| 2011/0082495 A1 | 4/2011 | Ruiz |
| 2011/0098525 A1 | 4/2011 | Kermode et al. |
| 2011/0218566 A1 | 9/2011 | van der Burg et al. |
| 2011/0301630 A1 | 12/2011 | Hendriksen et al. |
| 2012/0029553 A1 | 2/2012 | Quinn et al. |
| 2012/0035643 A1 | 2/2012 | Khairkhahan et al. |
| 2012/0065662 A1 | 3/2012 | van der Burg et al. |
| 2012/0125619 A1 | 5/2012 | Wood et al. |
| 2012/0172654 A1 | 7/2012 | Bates |
| 2012/0172927 A1 | 7/2012 | Campbell et al. |
| 2012/0239077 A1 | 9/2012 | Zaver et al. |
| 2012/0239083 A1 | 9/2012 | Kreidler |
| 2012/0245619 A1 | 9/2012 | Guest |
| 2012/0283585 A1 | 11/2012 | Werneth et al. |
| 2012/0283773 A1 | 11/2012 | Van Tassel et al. |
| 2012/0323267 A1 | 12/2012 | Ren |
| 2013/0006343 A1 | 1/2013 | Kassab et al. |
| 2013/0012982 A1 | 1/2013 | Khairkhahan et al. |
| 2013/0018413 A1 | 1/2013 | Oral et al. |
| 2013/0110154 A1 | 5/2013 | van der Burg et al. |
| 2013/0165735 A1 | 6/2013 | Khairkhahan et al. |
| 2013/0211492 A1 | 8/2013 | Schneider et al. |
| 2013/0331884 A1 | 12/2013 | Van der Burg et al. |
| 2014/0018841 A1 | 1/2014 | Peiffer et al. |
| 2014/0039536 A1 | 2/2014 | Cully et al. |
| 2014/0046360 A1 | 2/2014 | van der Burg et al. |
| 2014/0081314 A1 | 3/2014 | Zaver et al. |
| 2014/0100596 A1 | 4/2014 | Rudman et al. |
| 2014/0142612 A1 | 5/2014 | Li et al. |
| 2014/0148842 A1 | 5/2014 | Khairkhahan et al. |
| 2014/0163605 A1 | 6/2014 | VanTassel et al. |
| 2014/0188157 A1 | 7/2014 | Clark |
| 2014/0303719 A1 | 10/2014 | Cox et al. |
| 2014/0336612 A1 | 11/2014 | Frydlewski et al. |
| 2014/0336699 A1 | 11/2014 | van der Burg et al. |
| 2015/0005810 A1 | 1/2015 | Center et al. |
| 2015/0039021 A1 | 2/2015 | Khairkhahan et al. |
| 2015/0080903 A1 | 3/2015 | Dillard et al. |
| 2015/0133989 A1* | 5/2015 | Lubock ............ A61B 17/12109 |
| | | 606/200 |
| 2015/0196300 A1 | 7/2015 | Tischler et al. |
| 2015/0230909 A1 | 8/2015 | Zaver et al. |
| 2015/0238197 A1 | 8/2015 | Quinn et al. |
| 2015/0305727 A1 | 10/2015 | Karimov et al. |
| 2015/0313604 A1 | 11/2015 | Roue et al. |
| 2015/0313605 A1 | 11/2015 | Griffin |
| 2015/0327979 A1 | 11/2015 | Quinn et al. |
| 2015/0374491 A1 | 12/2015 | Kreidler |
| 2016/0051358 A1 | 2/2016 | Sutton et al. |
| 2016/0058539 A1 | 3/2016 | VanTassel et al. |
| 2016/0066922 A1 | 3/2016 | Bridgeman et al. |
| 2016/0106437 A1 | 4/2016 | van der Burg et al. |
| 2016/0192942 A1 | 7/2016 | Strauss et al. |
| 2016/0278784 A1 | 9/2016 | Edmiston et al. |
| 2016/0287259 A1 | 10/2016 | Hanson et al. |
| 2016/0331382 A1 | 11/2016 | Center et al. |
| 2016/0374657 A1 | 12/2016 | Kreidler |
| 2017/0027552 A1 | 2/2017 | Turkington et al. |
| 2017/0042550 A1 | 2/2017 | Chakraborty et al. |
| 2017/0056166 A1 | 3/2017 | Ratz et al. |
| 2017/0100112 A1 | 4/2017 | van der Burg et al. |
| 2017/0181751 A1 | 6/2017 | Larsen et al. |
| 2017/0340336 A1 | 11/2017 | Osypka |
| 2018/0064446 A1 | 3/2018 | Figulla et al. |
| 2018/0070950 A1 | 3/2018 | Zaver et al. |
| 2018/0140412 A1 | 5/2018 | Sutton et al. |
| 2018/0140413 A1 | 5/2018 | Quinn et al. |
| 2018/0250014 A1 | 9/2018 | Melanson et al. |
| 2019/0223883 A1 | 7/2019 | Anderson et al. |
| 2021/0015491 A1 | 1/2021 | Inouye et al. |
| 2022/0031333 A1 | 2/2022 | Zhou et al. |
| 2022/0338877 A1 | 10/2022 | Natesan et al. |

FOREIGN PATENT DOCUMENTS

| | | |
|---|---|---|
| CN | 106859722 A | 6/2017 |
| CN | 112773445 A | 5/2021 |
| DE | 10201004476 A1 | 3/2012 |
| EP | 1523957 A2 | 4/2005 |
| EP | 1595504 A1 | 11/2005 |
| EP | 2074953 A1 | 1/2009 |
| EP | 2481381 A1 | 8/2012 |
| EP | 2928420 A1 | 10/2015 |
| EP | 3072461 A1 | 9/2016 |
| EP | 3372173 A2 | 9/2018 |
| JP | 2003532457 A | 11/2003 |
| JP | 2005324019 A | 11/2005 |
| JP | 2007513684 A | 5/2007 |
| JP | 2009160402 A | 7/2009 |
| JP | 2012501793 A | 1/2012 |
| WO | 9313712 A1 | 7/1993 |
| WO | 9504132 A1 | 2/1995 |
| WO | 9522359 A1 | 8/1995 |
| WO | 9601591 A1 | 1/1996 |
| WO | 9640356 A1 | 12/1996 |
| WO | 9721402 A1 | 6/1997 |
| WO | 9726939 A1 | 7/1997 |
| WO | 9728749 A1 | 8/1997 |
| WO | 9735522 A1 | 10/1997 |
| WO | 9802100 A1 | 1/1998 |
| WO | 9817187 A1 | 4/1998 |
| WO | 9822026 A1 | 5/1998 |
| WO | 9823322 A1 | 6/1998 |
| WO | 9827868 A1 | 7/1998 |
| WO | 9905977 A1 | 2/1999 |
| WO | 9907289 A1 | 2/1999 |
| WO | 9908607 A1 | 2/1999 |
| WO | 9923976 A1 | 5/1999 |
| WO | 9925252 A1 | 5/1999 |
| WO | 9930640 A1 | 6/1999 |
| WO | 9944510 A1 | 9/1999 |
| WO | 9959479 A1 | 11/1999 |
| WO | 0001308 A1 | 1/2000 |
| WO | 0016705 A1 | 3/2000 |
| WO | 0027292 A1 | 5/2000 |
| WO | 0035352 A1 | 6/2000 |
| WO | 0053120 A1 | 9/2000 |
| WO | 0067669 A1 | 11/2000 |
| WO | 0108743 A1 | 2/2001 |
| WO | 0115629 A1 | 3/2001 |
| WO | 0121247 A1 | 3/2001 |
| WO | 0126726 A1 | 4/2001 |
| WO | 0130266 A1 | 5/2001 |
| WO | 0130267 A1 | 5/2001 |
| WO | 0130268 A1 | 5/2001 |
| WO | 0170119 A1 | 9/2001 |
| WO | 0215793 A2 | 2/2002 |
| WO | 0224106 A2 | 3/2002 |
| WO | 02071977 A2 | 9/2002 |
| WO | 03007825 A1 | 1/2003 |
| WO | 03008030 A2 | 1/2003 |
| WO | 03032818 A1 | 4/2003 |
| WO | 2004012629 A1 | 2/2004 |

(56) References Cited

FOREIGN PATENT DOCUMENTS

| WO | 2007044536 A1 | 4/2007 |
|---|---|---|
| WO | 2010024801 A1 | 3/2010 |
| WO | 2010081033 A1 | 7/2010 |
| WO | 2013060855 A1 | 5/2013 |
| WO | 2013159065 A1 | 10/2013 |
| WO | 2014011865 A1 | 1/2014 |
| WO | 2014018907 A1 | 1/2014 |
| WO | 2014089129 A1 | 6/2014 |
| WO | 2014106239 A1 | 7/2014 |
| WO | 2015164836 A1 | 10/2015 |
| WO | 2016087145 A1 | 6/2016 |
| WO | 2018017935 A1 | 1/2018 |
| WO | 2018187732 A1 | 10/2018 |
| WO | 2019084358 A1 | 5/2019 |
| WO | 2020163507 A1 | 8/2020 |

OTHER PUBLICATIONS

International Search Report and Written Opinion dated Aug. 3, 2004 for International Application No. PCT/US2004/008109.

International Search Report and Written Opinion dated Feb. 15, 2000 for International Application No. PCT/US99/26325.

International Search Report dated May 20, 2003 for International Application No. PCT/US02/33808.

Written Opinion dated Nov. 17, 2003 for International Application No. PCT/US/02/33808.

International Search Report and Written Opinion dated Aug. 21, 2018 for International Application No. PCT/US2018/029684.

Cragg et al., "A New Percutaneous Vena Cava Filter," American Journal of Radiology, Sep. 1983, pp. 601-604, vol. 141.

Cragg et al, "Nonsurgical Placement of Arterial Endoprostheses: A New Technique Using Nitinol Wire," Radiology, Apr. 1983, pp. 261-263, vol. 147, No. 1.

Lock et al., "Transcatheter Closure of Atrial Septal Defects." Circulation, May 1989, pp. 1091-1099, vol. 79, No. 5.

Lock et al., "Transcatheter Umbrella Closure of Congenital Heart Defects," Circulation, Mar. 1987, pp. 593-599, vol. 75, No. 3.

Rashkind et al., "Nonsurgical closure of patent ductus arteriosus: clinical application of the Rashkind PDA Occluder System," Circulation, Mar. 1987, pp. 583-592, vol. 75, No. 3.

Rosengart et al., "Percutaneous and Minimally Invasive Valve Procedures," Circulation, Apr. 1, 2008, pp. 1750-1767, vol. 117.

Ruttenberg, "Nonsurgical Therapy of Cardiac Disorders," Pediatric Consult, 1986, Pages not numbered, vol. 5, No. 2.

Sugita et al., "Nonsurgical Implantations of a Vascular Ring Prosthesis Using Thermal Shape Memory Ti/Ni Alloy (Nitinol Wire)," Trans. Am. Soc. Artif. Intern. Organs, 1986, pp. 30-34, vol. XXXII.

Wessel et al., "Outpatient Closure of the Patent Ductus Arteriousus," Circulation, 1988, pp. 1068-1071, vol. 77, No. 5.

Tung et al., U.S. Appl. No. 61/559,941, filed Nov. 15, 2011.

Yue Yu et al., U.S. Appl. No. 61/557,880, filed Dec. 20, 2011.

Cline, "File: Fish hooks.jpg," Wikipedia foundation , Inc., San Francisco, CA, Jun. 2007; p. 1 of 4; available online at http://en.wikipedia.org/wiki/File:Fish_hooks.jpg; last accessed Oct. 5, 2012.

International Search Report and Written Opinion dated Apr. 22, 2014 for International Application No. PCT/US2013/078454.

Aryana et al., "Incomplete Closure of the Left Atrial Appendage: Implication and Management." Curr Cardiol Rep., 18(9):82, 2016.

Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.

University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.

Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.

Romero et al., "Left Atrial Appendage Closure Devices," Clinical Medicine Insights: Cardiology, vol. 8, pp. 45-52, 2014.

Invitation to Pay Additional Fees and, Where Applicable, Protest Fee, for International Application No. PCT/US2016/043363, mailed Oct. 13, 2016.

International Search Report and Written Opinion dated Oct. 14, 2019 for International Application No. PCT/US2019/047452.

International Search Report and Written Opinion dated Oct. 27, 2017 for International Application No. PCT/US2017/048150.

International Search Report and Written Opinion dated Jan. 21, 2019 for International Application No. PCT/US2018/051953.

International Search Report and Written Opinion dated Oct. 13, 2016 for International Application No. PCT/US2016/043363.

International Search Report and Written Opinion dated Mar. 17, 2020, for International Application No. PCT/US2019/065243.

International Search Report and Written Opinion dated Sep. 9, 2019 for International Application No. PCT/US2019/033698.

Blackshear et al; "Appendage Obliteration to Reduce Stroke in Cardiac Surgical Patients with Atrial Fibrillation", Ann. Thoracic Surgery, pp. 755-759, 1996.

Lindsay, "Obliteration of the Left Atrial Appendage: A Concept Worth Testing", Ann. Thoracic Surgery, 1996.

Invitation to Pay Additional Fees dated Feb. 22, 2019 for International Application No. PCT/US2018/066163.

International Search Report and Written Opinion dated Oct. 23, 2020 for International Application No. PCT/US2020/042192.

* cited by examiner

MEDICAL DEVICE FOR OCCLUDING A LEFT ATRIAL APPENDAGE

CROSS REFERENCE TO RELATED APPLICATIONS

This application claims the benefit of priority of U.S. Provisional Application No. 63/356,535 filed Jun. 29, 2022, the entire disclosure of which is hereby incorporated by reference.

TECHNICAL FIELD

The present disclosure pertains to medical devices and systems, and methods for manufacturing and using medical devices and systems. More particularly, the present disclosure pertains to medical implants for occluding a left atrial appendage.

BACKGROUND

Diseases and/or medical conditions that impact the cardiovascular system are prevalent throughout the world. Traditionally, treatment of the cardiovascular system was often conducted by directly accessing the impacted part of the system. More recently, less invasive therapies have been developed, and have gained wide acceptance among patients and clinicians.

Atrial fibrillation is a common sustained cardiac arrhythmia affecting over 30 million people worldwide, according to some estimates. Atrial fibrillation is the irregular, chaotic beating of the upper chambers of the heart. Electrical impulses discharge so rapidly that the atrial muscle quivers or fibrillates. Episodes of atrial fibrillation may last a few minutes or several days. The most serious consequence of atrial fibrillation is ischemic stroke. It has been estimated that up to 20% of all strokes are related to atrial fibrillation. Most atrial fibrillation patients, regardless of the severity of their symptoms or frequency of episodes, require treatment to reduce the risk of stroke. The left atrial appendage is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage.

The disclosure relates to medical implants for occluding the left atrial appendage. Of the known medical devices, systems, and methods, each has certain advantages and disadvantages. There is an ongoing need to provide alternative medical devices and systems, as well as alternative methods for manufacturing and using medical devices and systems.

SUMMARY

In one example, a medical implant for occluding a left atrial appendage may comprise an expandable framework configured to shift between a first configuration and a second configuration, and an occlusive element secured to the expandable framework. The expandable framework may include a proximal hub and a plurality of interconnected struts extending from the proximal hub and joined together at a plurality of strut intersections. The plurality of interconnected struts may include a first plurality of struts and a second plurality of struts. In the second configuration, the first plurality of struts may each extend radially along a first strut path from the proximal hub to one of a first plurality of strut intersections. In the second configuration, the second plurality of struts may each extend radially along a second strut path from the proximal hub to one of a second plurality of strut intersections.

In addition or alternatively to any example described herein, the second plurality of strut intersections is disposed radially outward of the first plurality of strut intersections.

In addition or alternatively to any example described herein, the second plurality of strut intersections is disposed proximate a radially outermost extent of the expandable framework in the second configuration.

In addition or alternatively to any example described herein, each of the second plurality of struts is devoid of any other connections to the expandable framework between the proximal hub and the second plurality of strut intersections.

In addition or alternatively to any example described herein, the first strut path extends distally from the proximal hub to a first curve and then proximally from the first curve to one of the first plurality of strut intersections.

In addition or alternatively to any example described herein, the second strut path extends distally from the proximal hub to a first curve, proximally from the first curve to a second curve, distally from the second curve to a third curve, proximally from the third curve to a fourth curve coupled to one of the second plurality of strut intersections.

In addition or alternatively to any example described herein, a distalmost extent of the first curve of the first strut path is disposed distal of a distalmost extent of the first curve of the second strut path.

In addition or alternatively to any example described herein, the first curve of the first strut path is concave in a proximal direction and the second curve of the second strut path is concave in a distal direction such that the first curve of the first strut path opens toward a center of the second curve of the second strut path and the second curve of the second strut path opens toward a center of the first curve of the first strut path.

In addition or alternatively to any example described herein, the first strut path, via an additional segment of the plurality of interconnected struts, continues from one of the first plurality of strut intersections to one of the second plurality of strut intersections to define an extended first strut path.

In addition or alternatively to any example described herein, the extended first strut path, if straightened, defines a first length, and the second strut path, if straightened, defines a second length. The first length is substantially equal to the second length.

In addition or alternatively to any example described herein, in the second configuration, the first plurality of struts forms a depression opening in a proximal direction and the second plurality of struts extends proximally into the depression.

In addition or alternatively to any example described herein, in the second configuration, the second plurality of struts prevents the occlusive element from deflecting into the depression.

In addition or alternatively to any example described herein, a medical device system may comprise a catheter, a core wire movably disposed within a lumen of the catheter, and a medical implant for occluding a left atrial appendage releasably connected to a distal portion of the core wire. The medical implant may include an expandable framework configured to shift between a first configuration and a second configuration, and an occlusive element secured to the expandable framework. The expandable framework may include a proximal hub and a plurality of interconnected struts extending from the proximal hub and joined together at a plurality of strut intersections. The plurality of interconnected struts may include a first plurality of struts and a second plurality of struts. In the second configuration, the first plurality of struts may each extend radially along a first strut path from the proximal hub to one of a first plurality of strut intersections. In the second configuration, the second plurality of struts may each extend radially along a second strut path from the proximal hub to one of a second plurality of strut intersections.

In addition or alternatively to any example described herein, the expandable framework is disposed in the first configuration when the medical implant is disposed within the lumen of the catheter and the expandable framework is configured to shift toward the second configuration when the medical implant is disposed outside of the lumen of the catheter.

In addition or alternatively to any example described herein, the medical implant includes a plurality of anchor members extending radially outward from the expandable framework in the second configuration.

In addition or alternatively to any example described herein, at least some of the plurality of anchor members extend through the occlusive element.

In addition or alternatively to any example described herein, a medical implant for occluding a left atrial appendage may comprise an expandable framework configured to shift between a first configuration and a second configuration, and an occlusive element disposed on the expandable framework. The expandable framework includes a proximal hub and a plurality of interconnected struts extending from the proximal hub and joined together at a plurality of strut intersections. The plurality of interconnected struts includes a first plurality of struts and a second plurality of struts. In the second configuration, the first plurality of struts forms a depression in the expandable framework defined by a radially inward boundary and a radially outward boundary, and the depression extends distally between the radially inward boundary and the radially outward boundary and opens in a proximal direction. In the second configuration, the second plurality of struts extends into the depression.

In addition or alternatively to any example described herein, the depression has a depth measured distally from a plane coincident with a proximal end of the proximal hub and oriented perpendicular to a longitudinal axis extending through the proximal hub. The second plurality of struts extends proximally within the depression to within 50% of the depth from the plane.

In addition or alternatively to any example described herein, the second plurality of struts is integrally formed with the plurality of interconnected struts as a single monolithic structure.

In addition or alternatively to any example described herein, the second plurality of struts is formed separately from the plurality of interconnected struts and subsequently fixedly attached thereto.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figures 1, 2:
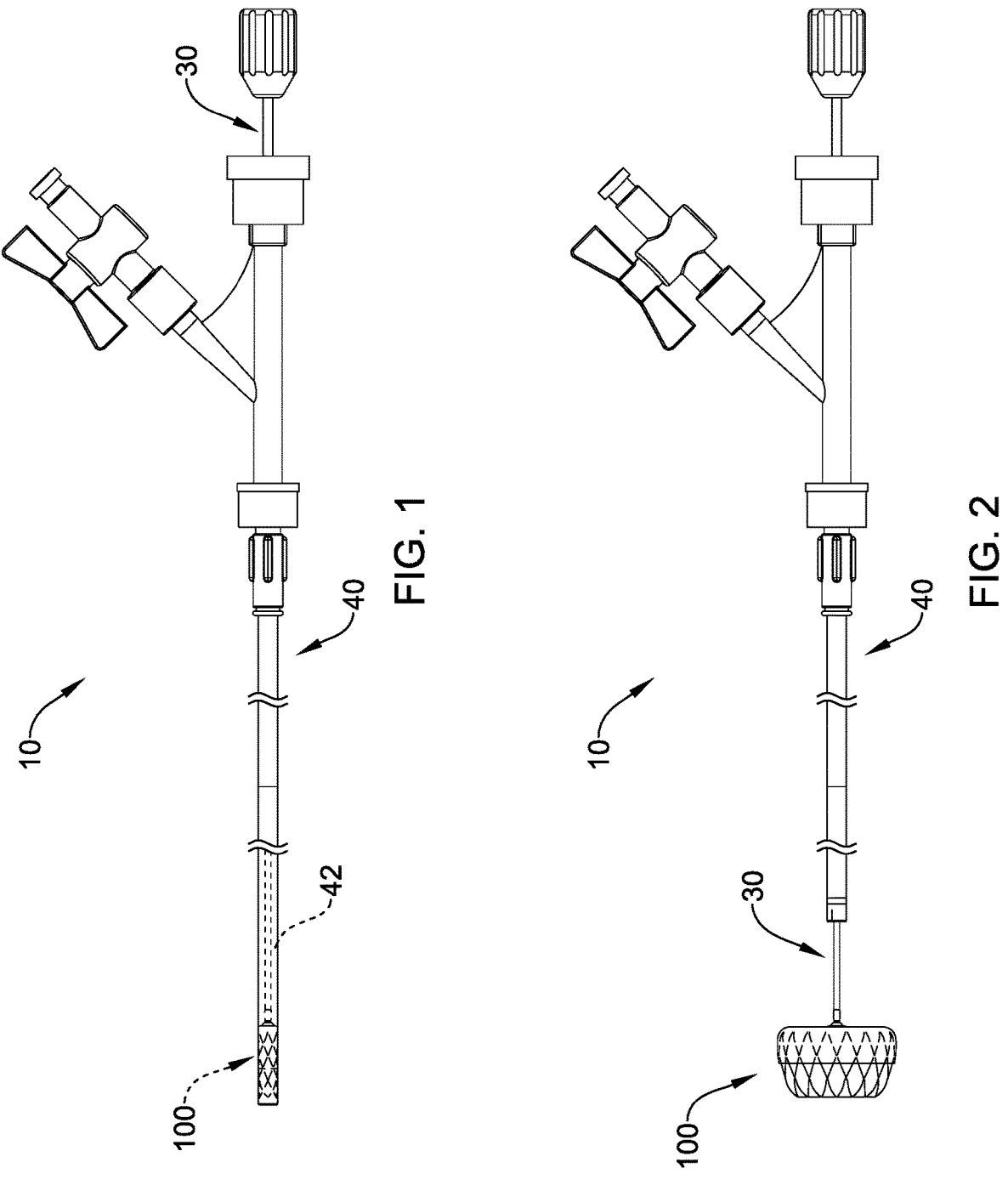
FIGS. 1-2 are side views of an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate exemplary aspects of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. It shall be understood that the discussion(s) herein may apply equally to any and/or all of the components for which there are more than one, unless explicitly stated to the contrary.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean the maximum outer dimension, "radial extent" may be understood to mean the maximum radial dimension, "longitudinal extent" may be understood to mean the maximum longitudinal dimension, etc. Each instance of an "extent" may be different (e.g., axial, longitudinal, lateral, radial, circumferential, etc.) and will be apparent to the skilled person from the context of the individual usage. In some instances, an "extent" may be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components and/or arrangements of medical implants, systems, and methods of manufacturing the same. It should be noted that in any given figure, some features of the medical implants, systems, and methods may not be shown, or may be shown schematically, for simplicity. Additional details regarding some elements may be illustrated in other figures in greater detail. The devices and/or methods disclosed herein may provide a number of desirable features and benefits as described in more detail below.

FIGS. 1-2 schematically illustrate selected components and/or arrangements of a medical device system 10. The medical device system 10 may be used to deliver and/or deploy a variety of medical implants (e.g., a cardiovascular medical implant, an occlusive medical implant, etc.) to one or more locations within the anatomy of a patient including but not limited to the heart and/or the vasculature.

The medical device system 10 may include a catheter 40 having a lumen 42 extending from a proximal opening to a distal opening, a core wire 30 movably and/or slidably disposed within the lumen 42, and a medical implant 100 (e.g., a cardiovascular medical implant, an occlusive medical implant, etc.). The medical implant 100 may be configured to occlude the left atrial appendage of the patient.

The medical implant 100 may include an expandable scaffold configured to shift between a first configuration (e.g., FIG. 1), wherein the medical implant 100 is disposed within the lumen 42 proximate the distal opening in the first configuration, and a second configuration (e.g., FIG. 2), wherein the medical implant 100 and/or the expandable scaffold is configured to shift between the first configuration and the second configuration when the medical implant 100 is disposed distal of the distal opening of the lumen 42 and/or the catheter 40, and/or when the medical implant 100 is unconstrained by the catheter 40.

The medical implant 100 may be disposed at and/or releasably connected to a distal portion of the core wire 30. In some embodiments, the example medical implant 100 may be releasably connected to the distal end of the core wire 30. The core wire 30 may be slidably and/or rotatably disposed within the lumen 42 of the catheter 40. In some embodiments, a proximal end of the core wire 30 may extend proximally of a proximal end of the catheter 40 and/or the proximal opening of the lumen 42 for manual manipulation by a clinician or practitioner.

Some suitable, but non-limiting, examples of materials for the medical device system 10, the core wire 30, the catheter 40, and/or the medical implant 100, etc. are discussed below. It is contemplated that any and/or all medical implants disclosed herein may be used in accordance with and/or be associated with the medical device system 10 described above.

Figure 3:
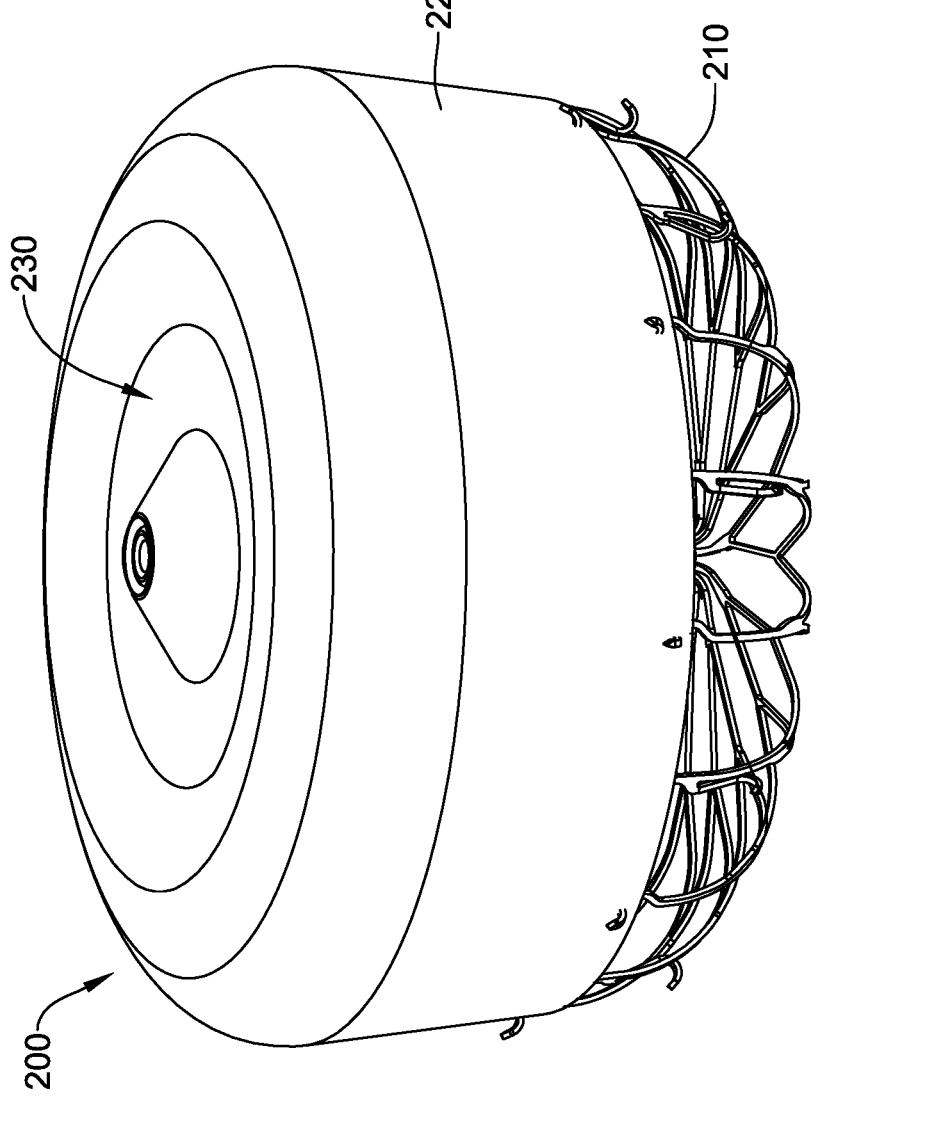
FIG. 3 is a perspective view of a prior art configuration of a medical implant.

FIG. 3 illustrates selected aspects of a prior art medical implant 200. The medical implant 200 includes a frame 210 and a covering 220. As shown in FIG. 3, the covering 220 may dip into a recess 230 formed in the frame 210 after deployment of the medical implant 200 because the covering 220 may be loose on the frame 210 to facilitate recapture and/or because the frame 210 was unable to fully expand and take up any slack in the covering 220 due to anatomical limitations. In such instances, hemodynamics may cause a fluttering in the covering 220 due to variations in pressure, flow, etc. within the patient as the heart beats. The flutter may lead to incomplete endothelization across the covering 220 and/or the formation of blood clots which may be detrimental to patient health. As such, it may be desirable to explore alternative configurations which may reduce and/or eliminate the potential for a loose covering and/or flutter to occur.

Figure 4:
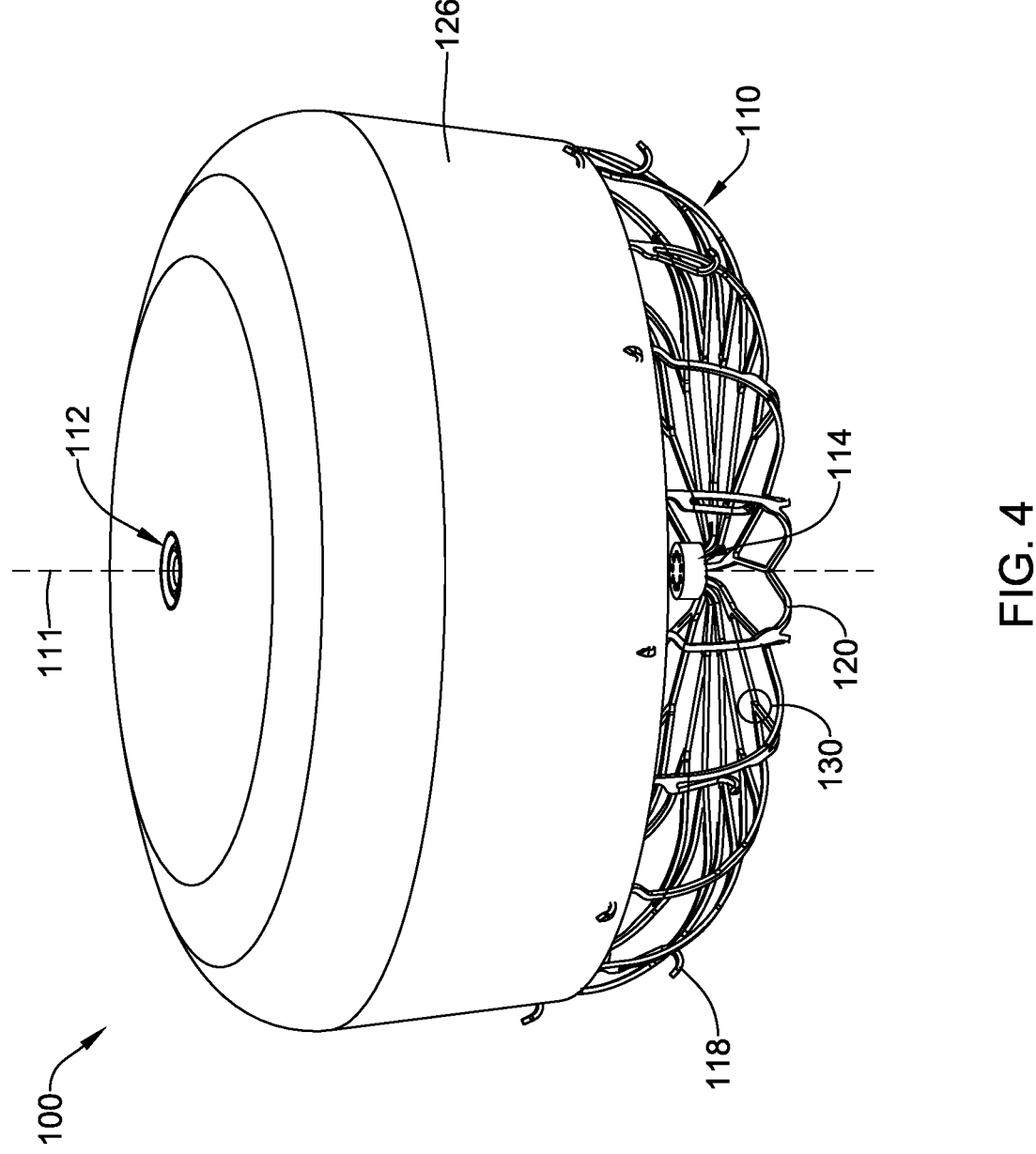
FIG. 4 is a perspective view illustrating selected aspects of a medical implant according to the disclosure.
Figure 5:
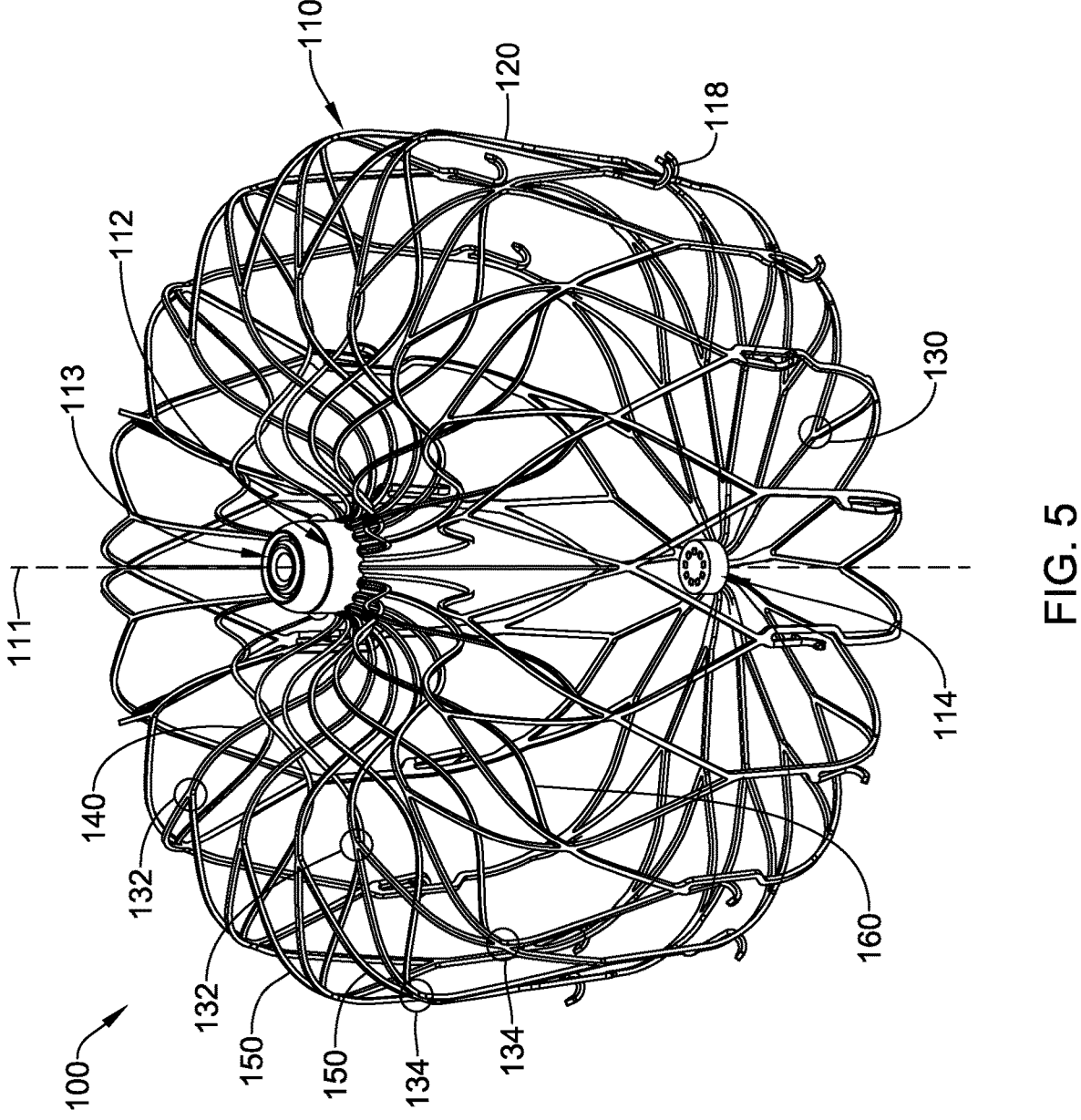
FIG. 5 illustrates selected aspects of the medical implant of FIG. 4.

FIGS. 4-5 illustrate selected aspects of the medical implant 100 according to the disclosure. The medical implant 100 includes an expandable framework 110 configured to shift between the first configuration (e.g., FIG. 1) and the second configuration (e.g., FIGS. 2, 4). The first configuration may be a radially collapsed configuration and the second configuration may be a radially expanded configuration. In some embodiments, the expandable framework 110 may include a proximal hub 112 and a plurality of interconnected struts 120 extending from the proximal hub 112. In some embodiments, the expandable framework 110 may include a proximal hub 112, a distal hub 114, and a plurality of interconnected struts 120 extending between the proximal hub 112 and the distal hub 114 and joined together at a plurality of strut intersections 130.

The expandable framework 110 may have a longitudinal axis 111 extending through the proximal hub 112. In some embodiments, the longitudinal axis 111 may extend from the proximal hub 112 to the distal hub 114. The proximal hub 112 of the expandable framework 110 may be configured to releasably attach or connect to the distal end of the core wire 30. The proximal hub 112 of the expandable framework 110 may include a threaded insert 113 fixedly attached to the expandable framework 110, the threaded insert 113 being configured to engage a threaded member disposed at the distal end of the core wire 30 of the medical device system 10 to releasably connect the medical implant 100 to the distal end of the core wire 30. The expandable framework

110 may be disposed in the first configuration when the medical implant 100 is disposed within the lumen 42 of the catheter 40 of the medical device system 10. The expandable framework 110 may be configured to shift toward the second configuration when the medical implant 100 is disposed outside of the lumen 42 of the catheter 40 of the medical device system 10 and/or when the medical implant 100 and/or the expandable framework 110 is unconstrained by the catheter 40.

The expandable framework 110 may include a plurality of anchor members 118 each having a free end extending radially outward in the second configuration and being connected to the expandable framework 110 at a base. The plurality of anchor members 118 is configured to engage a wall of a left atrial appendage in the second configuration.

The medical implant 100 includes an occlusive element 126 disposed on and/or secured to the expandable framework 110 and/or the plurality of interconnected struts 120. In some embodiments, at least some of the plurality of anchor members 118 extend through the occlusive element 126. In at least some embodiments, the occlusive element 126 may assume a generally planar configuration across a proximal end of the expandable framework 110 and/or the plurality of interconnected struts 120, as shown in FIG. 4, when the expandable framework 110 is in the second configuration.

In some embodiments, the occlusive element 126 may be supported by the expandable framework 110, as described herein. Without limitation, the plurality of interconnected struts 120 may include a first plurality of struts 140 and a second plurality of struts 160, as seen in FIG. 5. Additional pluralities of struts are also contemplated. The plurality of strut intersections 130 may include a first plurality of strut intersections 132 and a second plurality of strut intersections 134. The first plurality of strut intersections 132 and the second plurality of strut intersections 134 may be disposed distal of the proximal hub 112 in the first configuration, and the first plurality of strut intersections 132 and the second plurality of strut intersections 134 may be disposed radially outward relative to the proximal hub 112 in the second configuration, and wherein the second plurality of strut intersections 134 may be disposed radially outward from the first plurality of strut intersections 132 in the second configuration. In some embodiments, the second plurality of strut intersections 134 may be disposed proximate a radially outermost extent of the expandable framework 110 in the second configuration. The first plurality of strut intersections 132 and the second plurality of strut intersections 134 may be disposed proximal of the distal hub 114 in the first configuration and in the second configuration. In at least some embodiments, the second plurality of struts 160 and/or each of the second plurality of struts 160 may be devoid of any other connections to the expandable framework 110 between the proximal hub 112 and the second plurality of strut intersections 134.

Figure 6:
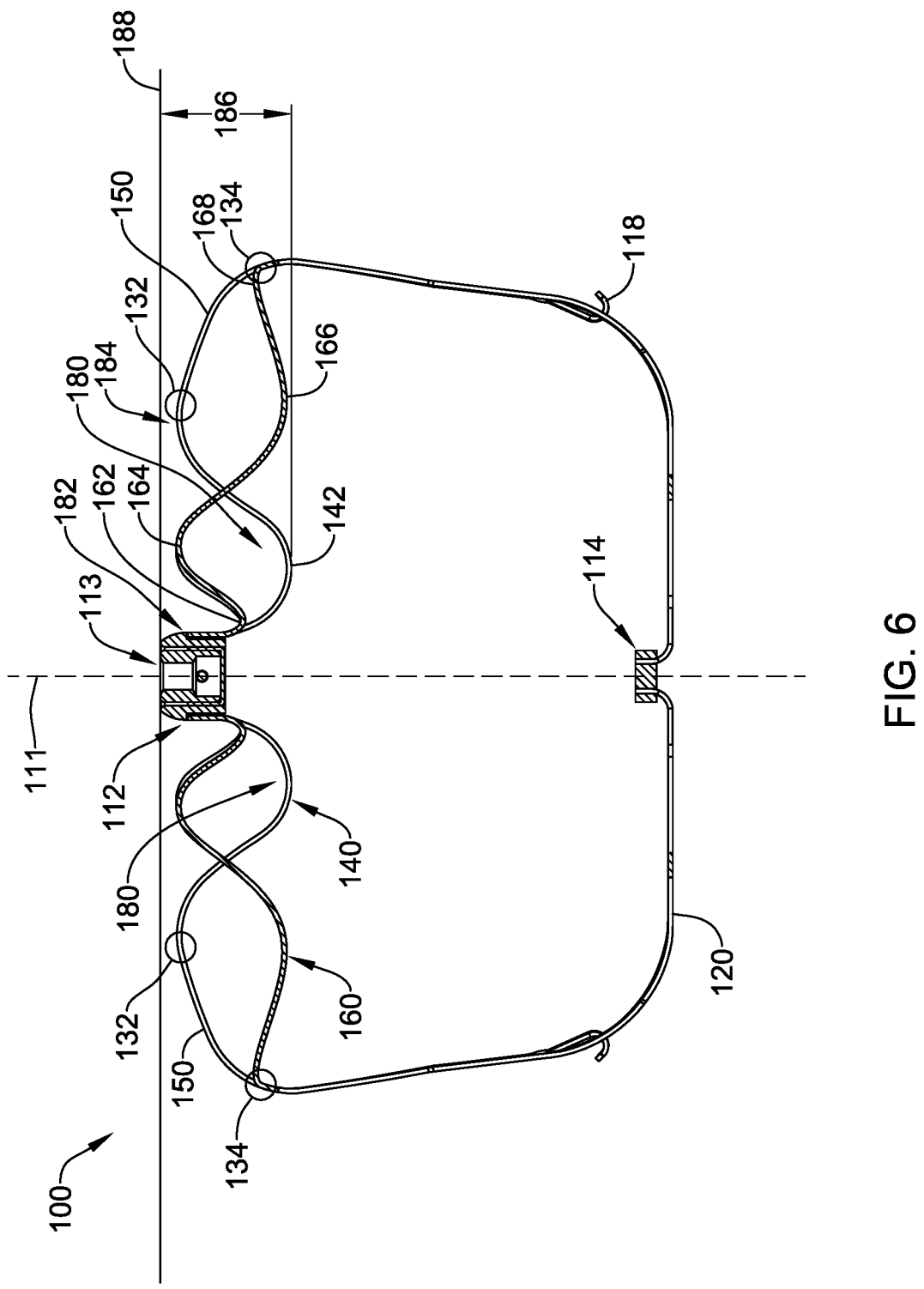
FIG. 6 is a side cross-sectional view illustrating selected aspects of the medical implant of FIG. 4.

As seen in FIGS. 5 and 6, in the second configuration, the first plurality of struts 140 forms a depression 180 in the expandable framework 110 opening in a proximal direction. The depression 180 may be defined by a radially inward boundary 182 and a radially outward boundary 184. The depression 180 may extend distally between the radially inward boundary 182 and the radially outward boundary 184 and open in the proximal direction. In the second configuration, the depression 180 may have a depth 186 measured distally from a plane 188 coincident with a proximal end of the proximal hub 112 and oriented perpendicular to the longitudinal axis 111 extending through the proximal hub 112 and/or from the proximal hub 112 to the distal hub 114, as shown in the partial cross-sectional view of FIG. 6. For clarity, some features of the expandable framework 110 have been removed from the view in FIG. 6 to facilitate discussion. For the purpose of discussion, the plane 188 may be disposed proximate a top of the depression 180 and the depth 186 may be measured to a bottom of the depression 180.

In the second configuration, the second plurality of struts 160 extends proximally into the depression 180. In some embodiments, in the second configuration, the second plurality of struts 160 extends proximally within the depression 180 to within 50% of the depth 186 from the plane 188. Described another way, in the second configuration, a proximalmost portion of the second plurality of struts 160 disposed within the depression 180 may extend within the depression 180 closer to the plane 188 and/or the top of the depression 180 than to the bottom of the depression 180. In some embodiments, in the second configuration, the second plurality of struts 160 extends proximally within the depression 180 to within 25% of the depth 186 from the plane 188. Other configurations are also contemplated. In the second configuration, the second plurality of struts 160 may prevent the occlusive element 126 from deflecting into the depression 180 formed by the first plurality of struts 140.

In the second configuration, the first plurality of struts 140 may each extend radially along a first strut path from the proximal hub 112 to one of the first plurality of strut intersections 132. In the second configuration, the second plurality of struts 160 may each extend radially along a second strut path from the proximal hub 112 to one of the second plurality of strut intersections 134.

In the second configuration, the first strut path may extend distally from the proximal hub 112 to a first curve 142 and then proximally from the first curve 142 to one of the first plurality of strut intersections 132. In the second configuration, the second strut path may extend distally from the proximal hub 112 to a first curve 162, proximally from the first curve 162 to a second curve 164, and distally from the second curve 164 to a third curve 166. In some embodiments, the second strut path may extend proximally from the third curve 166 to a fourth curve 168 coupled to one of the second plurality of strut intersections 134. In some embodiments, the fourth curve 168 of the second strut path may be connected directly to one of the second plurality of strut intersections 134. In some embodiments, a distalmost extent of the first curve 142 of the first strut path is disposed distal of a distalmost extent of the first curve 162 of the second strut path.

In some embodiments, the first curve 142 of the first strut path may be concave in a proximal direction (e.g., toward the plane 188) and the second curve 164 of the second strut path may be concave in a distal direction (e.g., away from the plane 188) such that the first curve 142 of the first strut path faces towards the second curve 164 of the second strut path. In some embodiments, the first curve 142 of the first strut path opens toward a center of the second curve 164 of the second strut path and the second curve 164 of the second strut path opens toward a center of the first curve 142 of the first strut path.

In some embodiments, in the second configuration, the first strut path, via an additional segment 150 of the plurality of interconnected struts 120, continues radially outward from one of the first plurality of strut intersections 132 to one of the second plurality of strut intersections 134 to define an extended first strut path. In at least some embodiments, the extended first strut path, if straightened, defines a first length 190 from the proximal hub 112 to one of the second plurality of strut intersections 134 (e.g., a combined length of the one of the plurality of first struts 140 and the additional segment 150), as shown in the detailed portion of the flat pattern view of FIG. 7. The second strut path, if straightened, defines a second length 192 from the proximal hub 112 to one of the second plurality of strut intersections 134 (e.g., a length of one of the second plurality of struts 160), as shown in the detailed portion of the flat pattern view of FIG. 7. In at least some embodiments, the first length 190 is substantially equal to the second length 192. Other configurations are also contemplated.

Figure 7:
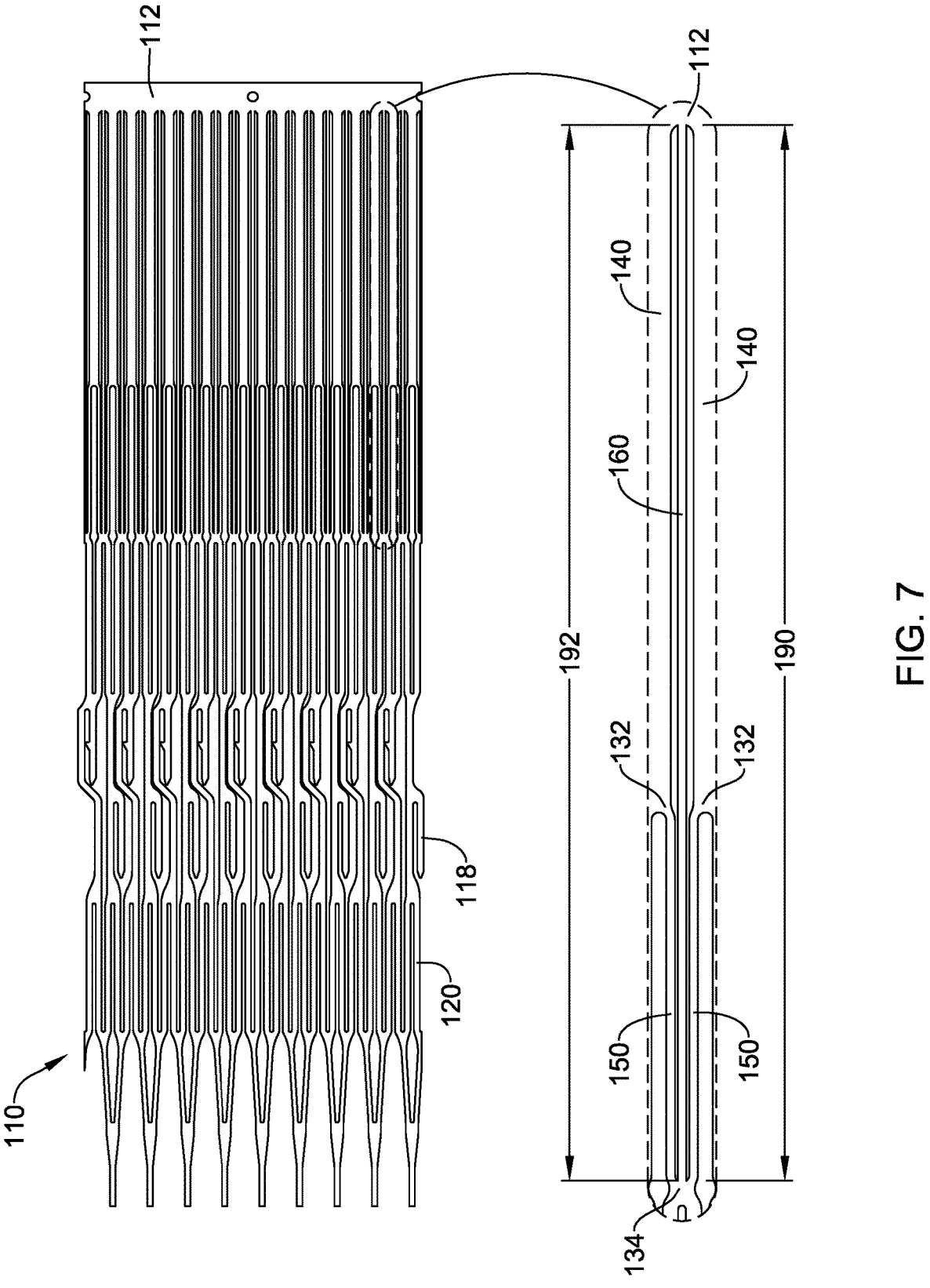
FIG. 7 illustrates a portion of a flat pattern of an expandable scaffold according to the disclosure.

As shown in FIG. 7, the plurality of interconnected struts 120 (e.g., the first plurality of struts 140 and/or the second plurality of struts 160) of the expandable framework 110 may be oriented generally parallel to each other and/or the longitudinal axis 111 of the expandable framework 110 in the first configuration. In some embodiments, each strut of the plurality of interconnected struts 120 (e.g., the first plurality of struts 140 and/or the second plurality of struts 160) of the expandable framework 110 may include and/or have its own longitudinal axis oriented generally parallel to the longitudinal axis 111 of the expandable framework 110 in the first configuration.

Figure 8:
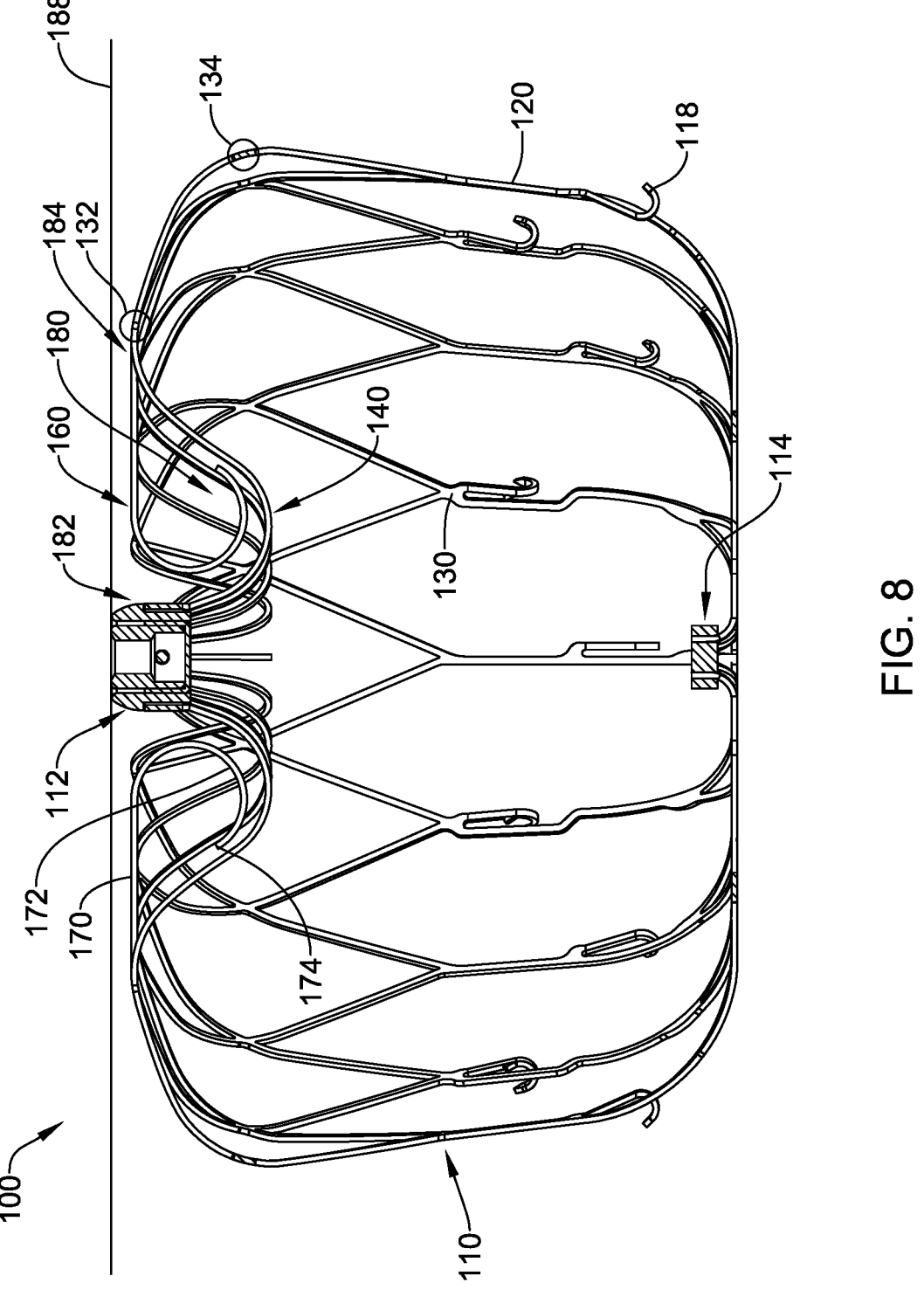
FIG. 8 illustrates selected aspects of an alternative configuration of the expandable scaffold of FIG. 6.
Figure 9:
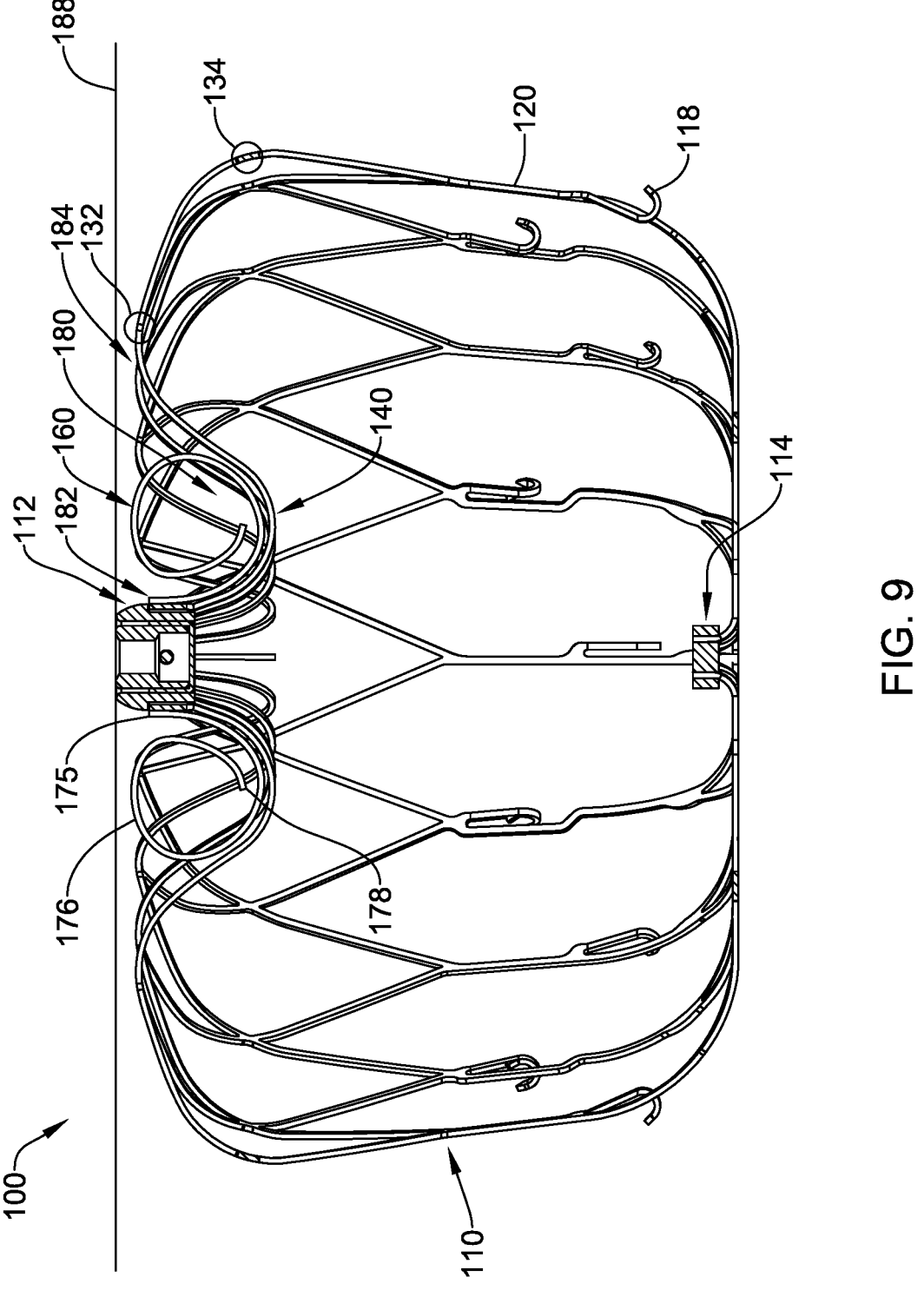
FIG. 9 illustrates selected aspects of an alternative configuration of the expandable scaffold of FIG. 6.

FIGS. 8-9 show alternative configurations of the medical implant 100 of FIGS. 4-6. The medical implant 100 may include the occlusive element 126 disposed on and/or secured to the expandable framework 110 and/or the plurality of interconnected struts 120. In FIGS. 8-9, the occlusive element 126 is not shown.

The plurality of interconnected struts 120 may include a first plurality of struts 140 and a second plurality of struts 160. Additional pluralities of struts are also contemplated. The plurality of strut intersections 130 may include the first plurality of strut intersections 132 described herein. In some embodiments, additional pluralities of strut intersections including but not limited to the second plurality of strut intersections 134 are also contemplated. The first plurality of strut intersections 132 may be disposed distal of the proximal hub 112 in the first configuration and the first plurality of strut intersections 132 may be disposed radially outward relative to the proximal hub 112 in the second configuration. The first plurality of strut intersections 132 may be disposed proximal of the distal hub 114 in the first configuration and in the second configuration.

As seen in FIGS. 8 and 9, in the second configuration, the first plurality of struts 140 forms a depression 180 in the expandable framework 110 opening in a proximal direction. The depression 180 may be defined by a radially inward boundary 182 and a radially outward boundary 184. The depression 180 may extend distally between the radially inward boundary 182 and the radially outward boundary 184 and open in the proximal direction. In the second configuration, the depression 180 may have a depth 186 measured distally from a plane 188 coincident with a proximal end of the proximal hub 112 and oriented perpendicular to the longitudinal axis 111 extending through the proximal hub 112 and/or from the proximal hub 112 to the distal hub 114. For clarity, some features of the expandable framework 110 have been removed from the view to facilitate discussion. For the purpose of discussion, the plane 188 may be disposed proximate a top of the depression 180 and the depth 186 may be measured to a bottom of the depression 180.

In the second configuration, the second plurality of struts 160 extends into the depression 180. In some embodiments, in the second configuration, a proximalmost extent of the second plurality of struts 160 extends within the depression 180 to within 50% of the depth 186 from the plane 188. Described another way, in the second configuration, a proximalmost portion of the second plurality of struts 160 disposed within the depression 180 may extend within the depression 180 closer to the plane 188 and/or the top of the depression 180 than to the bottom of the depression 180. In some embodiments, in the second configuration, the proximalmost extent of the second plurality of struts 160 extends within the depression 180 to within 25% of the depth 186 from the plane 188. In some embodiments, in the second configuration, the proximalmost extent of the second plurality of struts 160 extends within the depression 180 to within 10% of the depth 186 from the plane 188. Other configurations are also contemplated. In the second configuration, the second plurality of struts 160 may prevent the occlusive element 126 from deflecting into the depression 180 formed by the first plurality of struts 140.

In the second configuration, the first plurality of struts 140 may each extend radially along a first strut path from the proximal hub 112 to one of the first plurality of strut intersections 132. In the second configuration, the second plurality of struts 160 may each extend radially along a second strut path at least partially across the depression 180. In at least some embodiments, the second plurality of struts 160 and/or each of the second plurality of struts 160 may be attached and/or connected to the expandable framework 110 at a single point.

In the second configuration, the first strut path may extend distally from the proximal hub 112 to a first curve 142 and then proximally from the first curve 142 to one of the first plurality of strut intersections 132.

In some embodiments, the second plurality of struts 160 may be fixedly attached to the expandable framework 110 at one of the first plurality of strut intersections 132, as seen in FIG. 8. In some embodiments, the second plurality of struts 160 may be integrally formed with the expandable framework 110 and/or the plurality of interconnected struts 120 as a single monolithic structure. In some embodiments, the second plurality of struts 160 may be formed separately from the expandable framework 110 and/or the plurality of interconnected struts 120 and subsequently fixedly attached thereto. As such, the single point of attachment or connection of the second plurality of struts 160 and/or each of the second plurality of struts 160 to the expandable framework 110 and/or the plurality of interconnected struts 120 may be one of the first plurality of strut intersections 132.

In some embodiments, the second plurality of struts 160 may extend proximally from one of the first plurality of strut intersections 132 in the first configuration and the second plurality of struts 160 may extend radially inward from one of the first plurality of strut intersections 132 toward the proximal hub 112 in the second configuration. In some embodiments, in the second configuration, the second plurality of struts 160 may include a generally straight portion 170 extending radially inward from one of the first plurality of strut intersections 132 to a distal curl 172 curving distally away from the generally straight portion 170 and/or the plane 188 to a free end 174. The generally straight portion 170 may be configured to prevent the occlusive element 126 from deflecting into the depression 180 in the second configuration.

In some embodiments, the second plurality of struts 160 may be fixedly attached to the proximal hub 112 at a first end 175, as seen in FIG. 9. In some embodiments, the second plurality of struts 160 may be integrally formed with the expandable framework 110, the proximal hub 112, and/or the plurality of interconnected struts 120 as a single monolithic structure. In some embodiments, the second plurality of struts 160 may be formed separately from the expandable framework 110, the proximal hub 112, and/or the plurality of interconnected struts 120 and subsequently fixedly attached thereto. As such, the single point of attachment or connection of the second plurality of struts 160 and/or each of the second plurality of struts 160 to the expandable framework 110, the proximal hub 112, and/or the expandable framework 110 may be the proximal hub 112.

In some embodiments, the second plurality of struts 160 may extend distally from the proximal hub 112 in the first configuration and the second plurality of struts 160 may extend radially outward from the proximal hub 112 in the second configuration. In some embodiments, in the second configuration, the second plurality of struts 160 may extend distally and radially outward from the proximal hub 112 to a loop 176 curving proximally toward the plane 188 and radially inward toward the proximal hub 112 and then curving back distally away from the plane 188 to a free end 178. The loop 176 of the second plurality of struts 160 may be configured to prevent the occlusive element 126 from deflecting into the depression 180 in the second configuration.

A method of manufacturing the medical implant 100 may include forming and/or cutting the expandable framework 110 from a unitary tubular member in the first configuration. Alternatively, the method of manufacturing the medical implant 100 may include forming and/or cutting the expandable framework 110 from a flat sheet of material that is later rolled and/or formed into a tubular member. After forming the flat sheet of material into a tubular member, the tubular member may be welded or otherwise fixedly secured into a tubular shape. In some embodiments, forming and/or cutting the expandable framework 110 may be done via laser, waterjet, machining, etc. Other manufacturing methods and/or processes are also contemplated. It shall be understood that in some embodiments, forming and/or cutting the expandable framework 110 from a unitary tubular member may be preferred and illustration of a flat pattern does not constitute a preference for forming and/or cutting the expandable framework 110 from a flat sheet of material.

In some embodiments, the first plurality of struts 140 and/or the second plurality of struts 160 may be integrally formed with the plurality of interconnected struts 120 as a single monolithic structure to form the expandable framework 110. In some alternative embodiments, the second plurality of struts 160 may be formed separately from the plurality of interconnected struts 120 and subsequently fixedly attached thereto to form the expandable framework 110. In some embodiments, the second plurality of struts 160 may be fixedly attached to the plurality of interconnected struts 120 by welding, brazing, adhesive bonding, etc. Other configurations are also contemplated.

After forming and/or cutting the expandable framework 110, the method may include forming the expandable framework 110 into the second configuration. As part of forming the expandable framework 110 into the second configuration, the method may include bending each anchor member of the plurality of anchor members 118. In some embodiments, each anchor member may be bent individually. In some embodiments, two or more anchor members may be bent together as a group. In some embodiments, after forming the expandable framework 110 into the second configuration, the method may include heat setting the expandable framework 110 and/or the plurality of anchor members 118 in the second configuration. Other configurations and/or orders of operations are also contemplated.

In some embodiments, the method of manufacturing the medical implant 100 may include securing the occlusive element 126 to the expandable framework 110. In some embodiments, at least some of the plurality of anchor members 118 may extend through the occlusive element 126 in the second configuration. In some embodiments, the occlusive element 126 may be disposed on, along, and/or over an exterior surface of the expandable framework 110. In some embodiments, the occlusive element 126 may cover at least 20% of the expandable framework 110 in the second configuration. In some embodiments, the occlusive element 126 may cover at least 30% of the expandable framework 110 in the second configuration. In some embodiments, the occlusive element 126 may cover at least 40% of the expandable framework 110 in the second configuration. In some embodiments, the occlusive element 126 may cover at least 50% of the expandable framework 110 in the second configuration. In some embodiments, the occlusive element 126 may cover at least 60% of the expandable framework 110 in the second configuration. In some embodiments, the occlusive element 126 may cover at least 70% of the expandable framework 110 in the second configuration. Other configurations are also contemplated.

The materials that can be used for the various components of the medical implants, systems, and methods of manufacturing disclosed herein may include those commonly associated with medical devices. For simplicity purposes, the following discussion refers to the system. However, this is not intended to limit the system, devices, and/or methods described herein, as the discussion may be applied to other elements, members, components, or devices disclosed herein, such as, but not limited to, the expandable framework, the plurality of interconnected struts, the plurality of anchor members, the occlusive element, etc. and/or elements or components thereof.

In some embodiments, the system and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN®), polyether block ester, polyurethane (for example, Polyurethane 85A), polypropylene (PP), polyvinylchloride (PVC), polyether-ester (for example, ARNITEL®), ether or ester based copolymers (for example, butylene/poly(alkylene ether) phthalate and/or other polyester elastomers such as HYTREL®), polyamide (for example, DURETHAN® or CRISTAMID®), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID®), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, Elast-Eon® or ChronoSil®), biocompatible polymers, other suitable materials, or mixtures, combinations, copolymers thereof, polymer/metal composites, and the like. In some embodiments, the system and/or components thereof can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In some embodiments, portions or all of the system and/or components thereof may be doped with, made of, or otherwise include a radiopaque material. Radiopaque materials are understood to be materials capable of producing a relatively bright image on a fluoroscopy screen or another imaging technique (e.g., ultrasound, etc.) during a medical procedure. This relatively bright image aids a user in determining the location of the system. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MRI) compatibility is imparted into the system. For example, the system and/or components or portions thereof may be made of a material that does not substantially distort the image and create substantial artifacts (e.g., gaps in the image). Certain ferromagnetic materials, for example, may not be suitable because they may create artifacts in an MRI image. The system or portions thereof may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the system may include a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. In some embodiments, the yarns may be made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible system.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-protein and/or anti-bacterial agents (such as 2-methacryroyloxyethyl phosphorylcholine (MPC) and its polymers or copolymers); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical implant for occluding a left atrial appendage, comprising:
an expandable framework configured to shift between a first configuration and a second configuration;
wherein the expandable framework includes a proximal hub and a plurality of interconnected struts extending from the proximal hub and joined together at a plurality of strut intersections; and
an occlusive element disposed over the plurality of interconnected struts;
wherein the plurality of interconnected struts includes a first plurality of struts and a second plurality of struts;

wherein in the second configuration, the first plurality of struts each extend radially along a first strut path from the proximal hub to one of a first plurality of strut intersections and the first plurality of struts form a depression in the expandable framework opening in a proximal direction;
wherein in the second configuration, the second plurality of struts each extend radially along a second strut path from the proximal hub to one of a second plurality of strut intersections and are configured to prevent the occlusive element from deflecting into the depression formed by the first plurality of struts.

2. The medical implant of claim 1, wherein the second plurality of strut intersections are disposed radially outward of the first plurality of strut intersections.

3. The medical implant of claim 2, wherein the second plurality of strut intersections are disposed proximate a radially outermost extent of the expandable framework in the second configuration.

4. The medical implant of claim 3, wherein each of the second plurality of struts are devoid of any other connections to the expandable framework between the proximal hub and the second plurality of strut intersections.

5. The medical implant of claim 1, wherein the first strut path extends distally from the proximal hub to a first curve and then proximally from the first curve to one of the first plurality of strut intersections.

6. The medical implant of claim 5, wherein the second strut path extends distally from the proximal hub to a first curve, proximally from the first curve to a second curve, distally from the second curve to a third curve, proximally from the third curve to a fourth curve coupled to one of the second plurality of strut intersections.

7. The medical implant of claim 6, wherein a distalmost extent of the first curve of the first strut path is disposed distal of a distalmost extent of the first curve of the second strut path.

8. The medical implant of claim 6, wherein the first curve of the first strut path is concave in a proximal direction and the second curve of the second strut path is concave in a distal direction such that the first curve of the first strut path opens toward a center of the second curve of the second strut path and the second curve of the second strut path opens toward a center of the first curve of the first strut path.

9. The medical implant of claim 1, wherein the first strut path, via an additional segment of the plurality of interconnected struts, continues from one of the first plurality of strut intersections to one of the second plurality of strut intersections to define an extended first strut path.

10. The medical implant of claim 9, wherein the extended first strut path, if straightened, defines a first length, and the second strut path, if straightened, defines a second length;
wherein the first length is substantially equal to the second length.

11. The medical implant of claim 1, wherein and the second plurality of struts extends proximally into the depression.

12. A medical device system, comprising:
a catheter;
a core wire movably disposed within a lumen of the catheter; and
a medical implant for occluding a left atrial appendage releasably connected to a distal portion of the core wire;
wherein the medical implant includes an expandable framework configured to shift between a first configuration and a second configuration, and an occlusive element disposed over the expandable framework;

wherein the expandable framework includes a proximal hub and a plurality of interconnected struts extending from the proximal hub and joined together at a plurality of strut intersections;

wherein the plurality of interconnected struts includes a first plurality of struts and a second plurality of struts;

wherein in the second configuration, the first plurality of struts each extend radially along a first strut path from the proximal hub to one of a first plurality of strut intersections and the first plurality of struts form a depression in the expandable framework;

wherein in the second configuration, the second plurality of struts each extend radially along a second strut path from the proximal hub to one of a second plurality of strut intersections in order to prevent the occlusive element from deflecting into the depression formed by the first plurality of struts.

13. The medical device system of claim 12, wherein the expandable framework is disposed in the first configuration when the medical implant is disposed within the lumen of the catheter and the expandable framework is configured to shift toward the second configuration when the medical implant is disposed outside of the lumen of the catheter.

14. The medical device system of claim 12, wherein the medical implant includes a plurality of anchor members extending radially outward from the expandable framework in the second configuration.

15. The medical device system of claim 14, wherein at least some of the plurality of anchor members extend through the occlusive element.

16. A medical implant for occluding a left atrial appendage, comprising:

an expandable framework configured to shift between a first configuration and a second configuration; and an occlusive element disposed on the expandable framework;

wherein the expandable framework includes a proximal hub and a plurality of interconnected struts extending from the proximal hub and joined together at a plurality of strut intersections;

wherein the plurality of interconnected struts includes a first plurality of struts and a second plurality of struts;

wherein in the second configuration, the first plurality of struts forms a depression in the expandable framework defined by a radially inward boundary and a radially outward boundary, and the depression extends distally between the radially inward boundary and the radially outward boundary and opens in a proximal direction;

wherein in the second configuration, the second plurality of struts extends into the depression.

17. The medical implant of claim 16, wherein the depression has a depth measured distally from a plane coincident with a proximal end of the proximal hub and oriented perpendicular to a longitudinal axis extending through the proximal hub;

wherein the second plurality of struts extends proximally within the depression to within 50% of the depth from the plane.

18. The medical implant of claim 16, wherein the second plurality of struts are integrally formed with the plurality of interconnected struts as a single monolithic structure.

19. The medical implant of claim 16, wherein the second plurality of struts are formed separately from the plurality of interconnected struts and subsequently fixedly attached thereto.

* * * * *